United States Patent
Lozano Castro et al.

(10) Patent No.: US 10,059,998 B2
(45) Date of Patent: Aug. 28, 2018

(54) MICRORNA SIGNATURE AS AN INDICATOR OF THE RISK OF EARLY RECURRENCE IN PATIENTS WITH BREAST CANCER

(71) Applicants: UNIVERSIDAD DE MÁLAGA, Málaga (ES); SERVICIO ANDALUZ DE SALUD, Seville (ES); FUNDACIÓN PÚBLICA ANDALUZA PARA LA INVESTIGACIÓN DE MÁLAGA EN BIOMEDICINA Y SALUD (FIMABIS), Málaga (ES)

(72) Inventors: José Lozano Castro, Málaga (ES); Emilio Alba Conejo, Málaga (ES); Luis Gustavo Pérez Rivas, Málaga (ES); José Jerez Aragonés, Málaga (ES); Nuria Ribelles Entrena, Seville (ES)

(73) Assignees: Servicio Andaluz de Salud, Sevilla (ES); Fundacion Publica Andaluza para la Investigacion de Malaga en Biomedicina y Salud (FIMABIS), Malaga (ES); Universidad de Malaga, Malaga (ES)

( * ) Notice: Subject to any disclaimer, the term of this patent is extended or adjusted under 35 U.S.C. 154(b) by 0 days.

(21) Appl. No.: 15/125,714

(22) PCT Filed: Mar. 13, 2015

(86) PCT No.: PCT/ES2015/070179
§ 371 (c)(1),
(2) Date: Sep. 13, 2016

(87) PCT Pub. No.: WO2015/136141
PCT Pub. Date: Sep. 17, 2015

(65) Prior Publication Data
US 2017/0002424 A1    Jan. 5, 2017

(30) Foreign Application Priority Data
Mar. 13, 2014    (ES) .................................. 201430349

(51) Int. Cl.
*A61K 48/00*    (2006.01)
*C07H 21/02*    (2006.01)
*C07H 21/04*    (2006.01)
*C12Q 1/6886*   (2018.01)

(52) U.S. Cl.
CPC ...... *C12Q 1/6886* (2013.01); *C12Q 2600/112* (2013.01); *C12Q 2600/118* (2013.01); *C12Q 2600/158* (2013.01); *C12Q 2600/178* (2013.01)

(58) Field of Classification Search
CPC .. C12N 15/113; C12N 2310/11; A61K 31/713
See application file for complete search history.

(56) References Cited

U.S. PATENT DOCUMENTS

7,638,612 B2 * 12/2009 Rashtchian ........ C12N 15/1096
435/6.11
2013/0190386 A1    7/2013 Croce et al.

FOREIGN PATENT DOCUMENTS

| EP | 2682477 A1 | 1/2014 | |
|---|---|---|---|
| WO | WO 2011/057003 A2 * | 5/2011 | ........... C12N 15/113 |
| WO | WO-2011094335 A2 | 8/2011 | |
| WO | WO-2011110644 A1 | 9/2011 | |
| WO | WO-2013057567 A1 | 4/2013 | |

OTHER PUBLICATIONS

Gee et al., The small-nucleolar RNAs commonly used for microRNA normalisation correlate with tumour pathology and prognosis, British Journal of Cancer, 2011, 104, 1168-1177.*
International Search Report and Written Opinion in corresponding International Application No. PCT/ES2015/070179 dated Jun. 19, 2015.
Ota et al., "Identification of recurrence-related microRNAs in the bone marrow of breast cancer patients," Int J Oncol. 38(4):955-62 (2011).
Pérez-Rivas et al., "A microRNA signature associated with early recurrence in breast cancer," PLoS One. 9(3):e91884 (2014).
Zhou et al., "MicroRNA-9 as potential biomarker for breast cancer local recurrence and tumor estrogen receptor status," PLoS One. 7(6):e39011 (2012).

* cited by examiner

*Primary Examiner* — Amy H Bowman
(74) *Attorney, Agent, or Firm* — McCarter & English, LLP; Jill Ann Mello

(57) ABSTRACT

The invention relates to the field of oncology and cancer treatment. The invention relates to methods for predicting the risk of recurrence of breast tumors using the expression signature of particular miRNAs. Specifically, the invention relates to a method for determining the risk of recurrence of breast cancer which comprises measuring the expression levels of at least one miRNA selected from the group consisting of miR-149-5p (SEQ ID NO: 1), miR-10a-5p, (SEQ ID NO: 2), miR-20b-5p, (SEQ ID NO: 3), miR-30a-3p (SEQ ID NO: 4), and miR-342-5p, (SEQ ID NO: 5) in a sample of the tumor, wherein a change in the expression level of at least one miRNA in the tumor with respect to the expression level in a control sample is indicative of a high risk of recurrence of the tumor. The invention also relates to tools and kits for carrying out the method of the invention.

28 Claims, 7 Drawing Sheets
Specification includes a Sequence Listing.

MICRORNA SIGNATURE AS AN INDICATOR OF THE RISK OF EARLY RECURRENCE IN PATIENTS WITH BREAST CANCER

RELATED APPLICATIONS

This application is a 35 U.S.C. § 371 national stage filing of International Application No. PCT/ES2015/070179, filed on Mar. 13, 2015, which claims priority to Spanish Patent Application No. P201430349, filed on Mar. 13, 2014. The entire contents of each of the foregoing applications are incorporated herein by reference.

FIELD OF THE INVENTION

The invention relates to the field of oncology and cancer treatment and prognosis. The invention includes methods for predicting the risk of recurrence of breast tumors using the expression signature of particular miRNAs.

INTRODUCTION

Breast cancer constitutes a group of heterogeneous diseases that can be classified based on both their clinical and molecular characteristics [1-5]. Breast cancer is the most common invasive cancer in women worldwide. Improvements in the early detection of primary tumors and the development of new therapies, together with the systemic use of adjuvant chemotherapy, have drastically reduced death rates and increased disease-free survival (DFS) in breast cancer. However, about one third of patients subjected to the removal of a breast tumor will develop metastasis, which is the biggest threat to survival associated with the tumor, which is closely associated with a worse prognosis [6, 7].

Cancer is called recurrent when it reappears after treatment. Recurrence can be local (in the same breast or in the mastectomy scar) or in a remote area.

The risk of relapse (or recurrence) after tumor resection is not constant over time. A detailed analysis of long-term follow-up studies in the past two decades reveals a bimodal risk function with two early and late recurrence peaks occurring after 1.5 and 5 years, respectively, followed by a virtually flat plateau wherein the risk of recurrence leans towards zero [8-10].

Some researchers have posited a causal relationship between surgery on the tumor and the bimodal recurrence pattern (i.e., an iatrogenic effect) [11]. According to that model, the surgical removal of the primary breast tumor would accelerate the growth of latent metastatic foci, disrupting the balance between circulating pro- and anti-angiogenic factors [9, 11-14]. This hypothesis is supported by the fact that the two peaks in relapse are observed independently of other factors, separately from the surgery, such as the condition of the axillary lymph glands, the type of surgery or the administration of adjuvant therapy. Although the estrogen receptor (ER)-negative tumors are associated with a higher risk of early recurrence [15], the bimodal distribution pattern is observed regardless of the condition of hormone receptors [16].

Therefore, according to this bimodal risk function model, early recurrence can be explained as an iatrogenic effect of the surgical removal of the primary tumor. In contrast, late recurrences are not synchronized, and it is therefore though that they are not affected by the surgical procedure. Instead, it is posited that they are the result of the sudden spread of the micrometastasis of a single cell during the natural progression of the disease [11]. According to this hypothesis, earlier reports have centered their attention on the foci of latent metastases, the surrounding microenvironment of the tumor or even signals present in serum to find factors that could explain the different risks of recurrence.

Other studies also suggest that the tumor relapse dynamics can be a consequence of the surgical intervention for removing the primary tumor, which could disrupt circulating levels of VEGF, TNFα and other inflammatory cytokines [17-19]. However, empirical evidence proving a molecular connection between surgery on the primary breast tumor and the bimodal recurrence pattern has yet to be found.

It has generally been reported that some biological factors are involved in several particular types of cancers, including somatic mutations of specific genes, changed protein expression, changed protein activation, and changed gene expression models.

The identification of distinctive expression patterns based on the gene expression profile by means of gene profiling methods, such as a microarray, has given rise to a breast tumor classification comprising five different subtypes: luminal A, luminal B, tumors overexpressing HER2 (HER2+), basal-like and normal type [3, 4]. This classification has been adopted in routine clinical practice, defining intrinsic subtypes with different histological features, response to pharmacological treatment and clinical results [3, 20-23]. The HER2+ and basal-like subtypes are commonly associated with a higher risk of recurrence, whereas luminal tumors are often linked with a longer tumor-free survival [24-26].

A recent study conducted by the Molecular Taxonomy of Breast Cancer International Consortium (METABRIC) has put forth a new genome-based classification by means of integrating both genomic and transcriptomic data. This new molecular stratification is based on the impact of the copy number aberrations (CNAs) in the transcriptome and classifies breast tumors in 10 integrative clusters (IntClusts 1-10), each associated with different clinical results [27, 28].

MicroRNAs (or miRNAs) are small, single-stranded RNA molecules that play an important role in the regulation of gene expression [29, 30]. They are transcribed as large RNA precursors (PRI-miRNAs) that are processed sequentially in the nucleus to produce an RNA hairpin with 65 nucleotides (nt), referred to as precursor-miRNA (pre-miRNA), and in the cytoplasm to produce a mature and active miRNA with 19-23 nt [31-33].

miRNAs generally act as negative modulators of gene expression. miRNAs bind to a partially complementary sequence generally located in the 3' untranslated region (3'-UTR) of their target mRNA and inhibit its translation [34]. Due to this partial complementarity, a single miRNA can be directed to multiple transcripts therefore down-regulating the expression of many proteins in the same or different pathway [29]. 1,872 miRNA precursors and 2,578 mature miRNAs have currently been identified in the human genome (miRBase 20, www.mirbase.org) [35], although the biological role of most of them is not known in detail.

As occurs with mRNA expression, the transcriptional profile of miRNAs can vary between the different tissues and stages of development. Changes in expression patterns of miRNA and its sequences are common in several diseases, including cancer [36, 37]. miRNAs are involved in many deregulated pathways in tumor cells, particularly those related to tumor markers [38, 39] and often located in breakpoint regions which are enlarged, eliminated or translocated in cancer [36]. Several miRNAs exhibit oncogenic activity (oncomiRs) or tumor-suppressing activity (TS-MIR) and can therefore contribute to tumorigenesis, tumor progression and metastasis [40-42].

Furthermore, miRNA expression profiles can provide molecular information that is clinically relevant in cancer [43]. In that sense, tumors of different origins can be classified according to specific miRNA expression patterns (also known as "miRNA signatures").

Different subtypes of one and the same tumor can also be distinguished by the miRNA expression pattern, and in some cases this expression pattern also provides a predictive value in clinical assessment [37, 44-46]. Therefore, by means of two types of approach in breast cancer, i.e., miRNA profiling and functional analysis, improvement of the knowledge about some molecular markers associated with breast cancer has been possible.

MicroRNAs are generally well preserved in a wide range of sample types, including bodily fluids and formalin-fixed paraffin-embedded (FFPE) tissues [47]. Several miRNAs have been linked with breast cancer metastasis [48, 49].

As previously indicated, any given miRNA has a wide range of different targets (in some estimations, about 200 targets per miRNA on average), and a given miRNA is usually involved in the plurality of different cellular pathways. Estimations of the risk of recurrence, decisions about treatment and the response to treatment have primarily been based on the stage of the tumor up until now. Until the present time, it was impossible to predict which miRNA might be associated with early recurrence (in the first two years, which is the recurrence having a worse prognosis) of a specific tumor.

The prediction of early recurrence in breast tumors constitutes an important challenge in clinical practice because early recurrence often corresponds to a more aggressive tumor, with fewer therapeutic options and a more discouraging prognosis. In fact, up to half of all relapses take place in the early peak of recurrence described by Demicheli et al. [16]. There is therefore a need to identify reliable biomarkers in patients who are suffering/have suffered from breast cancer, which would allow predicting the risk of recurrence of the tumor after surgery or a specific treatment; it would also help in choosing a suitable therapy or suitable follow-up for these individuals, and it would therefore ultimately help in prolonging the life or improving the quality of life of the patient. Furthermore, it would be necessary to identify new therapeutic targets as well as new medicinal products for preventing or treating recurrent breast cancer.

TERMS AND ABBREVIATIONS

DNA Deoxyribonucleic acid
mRNA Messenger RNA
ER Estrogen receptors
PRI-miRNAs RNA precursors
nt Nucleotides
pre-miRNA Precursor-miRNA
3'-UTR 3' untranslated region
FFPE Formalin-fixed paraffin-embedded
miRNA MicroRNA
miR MicroRNA
RNA Ribonucleic acid
RQ-PCR Real-time quantitative PCR
SEQ Sequence
cDNA Complementary DNA
RFS Recurrence-free survival
ROC Receiver Operating Characteristic

BRIEF DESCRIPTION OF THE INVENTION

As described in further detail below, microRNAs (miRNAs) are short non-coding RNA molecules that work as post-translational regulators of gene expression.

The inventors have identified five miRNAs as biomarkers for predicting the risk of recurrence of breast cancer in patients with breast cancer.

A first aspect of the present invention therefore relates to a method for predicting the risk of recurrence of breast cancer in a subject which comprises measuring the expression levels of at least one miRNA selected from the group consisting of:
    miR-149-5p (SEQ ID NO: 1)
    miR-10a-5p, (SEQ ID NO: 2)
    miR-20b-5p, (SEQ ID NO: 3)
    miR-30a-3p (SEQ ID NO: 4); and
    miR-342-5p, (SEQ ID NO: 5)
in a sample of the tumor, wherein a drop in the expression level of at least one miRNA in the tumor with respect to a control is indicative of a high risk of recurrence of the tumor.

In a second aspect, the invention provides a method for classifying a human subject suffering from breast cancer into one of two groups, wherein group 1 comprises the subjects that can be identified as being at a high risk of early recurrence by means of the method of the invention described above, and wherein group 2 represents the remaining subjects.

The invention furthermore provides pharmaceutical compositions, medicinal products, antibodies, and generally any type of therapy suitable for treating a human subject from group 1 that can be identified by means of the method described above.

In a third aspect, the present invention provides a method for predicting the survival of a subject with breast cancer which comprises measuring the expression levels of at least one miRNA selected from the group consisting of:
    miR-149-5p (SEQ ID NO: 1)
    miR-10a-5p, (SEQ ID NO: 2)
    miR-20b-5p, (SEQ ID NO: 3)
    miR-30a-3p (SEQ ID NO: 4); and
    miR-342-5p, (SEQ ID NO: 5)
in a sample of the tumor, wherein a drop in the expression level of at least one miRNA in the tumor with respect to a control is indicative of a low survival.

In a fourth aspect, the invention provides a kit comprising at least five oligonucleotides, characterized in that the five oligonucleotides are selected from the group consisting of five oligonucleotides capable of hybridizing with any one of two or more, and preferably all of the miRNAs or their cDNAs as defined in SEQ ID NOs: 1 to 5 in stringent conditions.

In a fifth aspect, the invention furthermore provides a miRNA as defined in the following sequences: SEQ ID NO: 1 (miR-149-5p); SEQ ID NO: 2 (miR-10a-5p); SEQ ID NO: 3 (miR-20b-5p); SEQ ID NO: 4 (miR-30a-3p); SEQ ID NO: 5 (miR-342-5p) for use in a method of treatment for breast cancer, or alternatively for use in a method of preventing the recurrence of breast cancer in a subject who is suffering or has suffered from breast cancer.

BRIEF DESCRIPTION OF THE DRAWINGS

Speed, T P (2003). "Exploration, normalization, and summaries of high density oligonucleotide array probe level data." Biostatistics 4 (2): 249-64. PMID 12925520.). Once all the microarrays have been corrected by means of RMA, expression data is compared. The data varying little in the population is used as a control. So said FIG. 1 shows the values of two RNAs, RNU48 and miR16, which are relatively constant in the patient population (1 patient=1 microarray).

Group 1 includes most luminal and/or non-recurrent tumors, whereas group 2 for the most part includes basal-like and/or early recurrence tumors.

Figure 3:
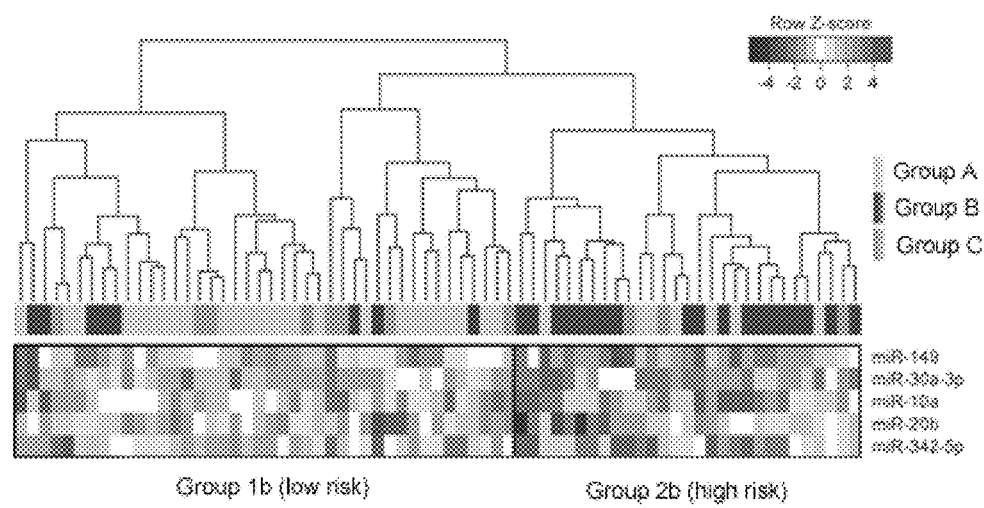

FIG. 3 shows that the miRNA expression profile is associated with early recurrence in breast cancer. Hierarchical cluster of 71 samples of tumors based on the expression profile of five miRNAs. It must be taken into account that the lowest expression levels of the five miRNAs define a different group, cluster 2b in the figure, primarily including tumors of "high risk" patients (group B). In contrast, most patients with a good prognosis (group A) have tumors with expression levels of the five miRNAs that are normal or higher than normal expression levels, defining a different group, cluster 1b in the figure ("low risk").

Figure 4:
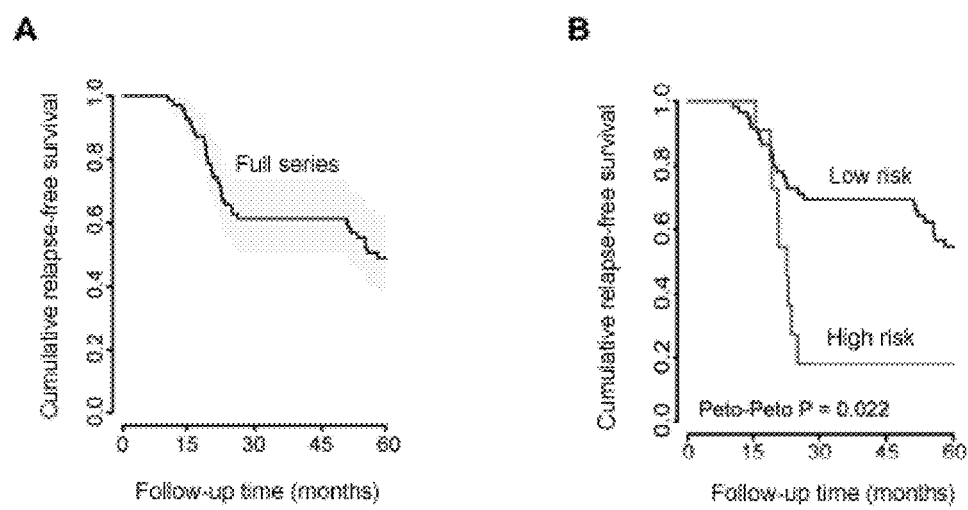

FIG. 4 shows that the expression profile of the five miRNAs discriminates patients with a different recurrence-free survival (RFS). A) Kaplan-Meier graph for the entire cohort of patients included in this study. B) Those patients whose tumors showed a drop in the expression levels of the five miRNAs (i.e., patients in cluster 2b, FIG. 3) were classified as "high risk" (light gray line) and their cumulative RFS was calculated (light gray line). The RFS was also calculated for the other patients of the cohort ("low risk," dark gray line). The Kaplan-Meier graph shows that the expression of the five miRNAs specifically discriminates tumors with a higher overall risk of early recurrence.

Figure 5:
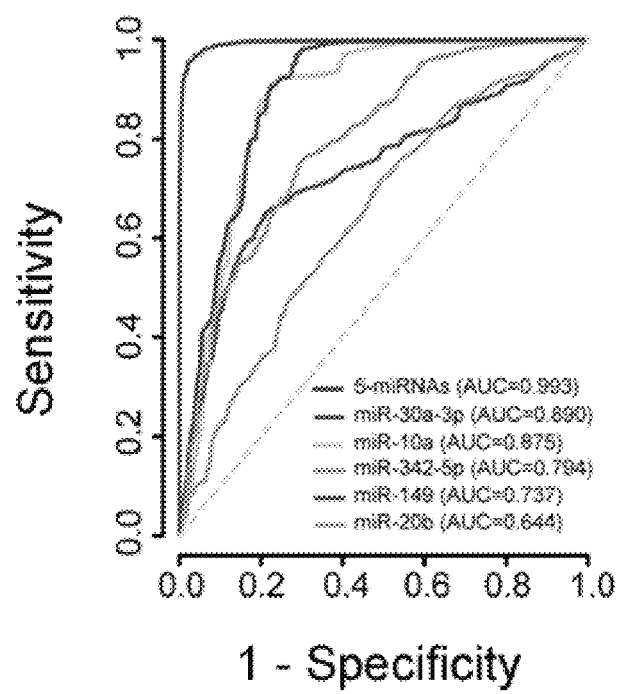

FIG. 5 shows a ROC (Receiver Operating Characteristic) curve for the early recurrence of breast cancer according to the expression levels of five miRNAs. The ROC curves generated using information about the prognosis and the expression levels of the five miRNAs can discriminate between patients who will develop an early recurrence and those who will remain disease-free. It must be taken into account that, despite the fact that miR-30-3p and miR-10a-5p have a high area under the curve (AUC) value, the expression levels of the five miRNAs have the most sound predictive value (AUC=0.993) for discriminating those patients with a high risk of presenting an early recurrence (group B in this cohort).

Figure 6:
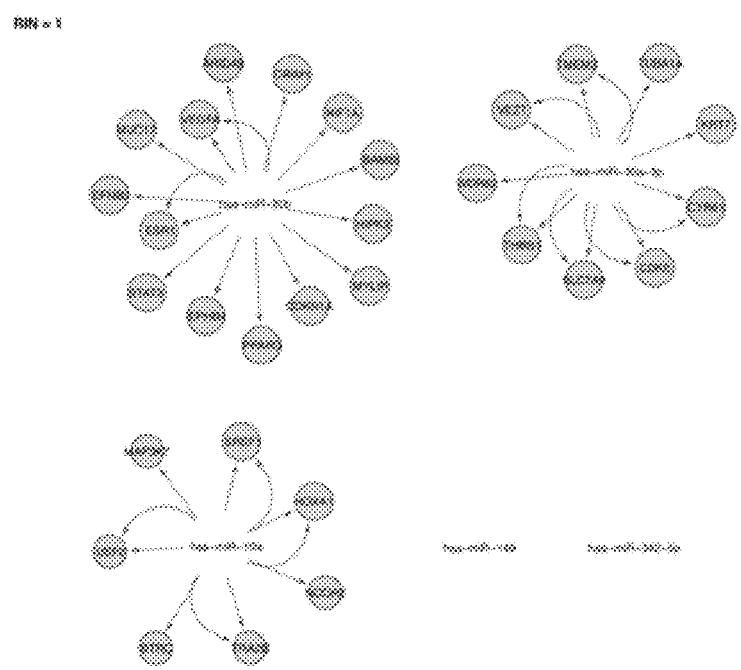

FIG. 6 shows the prediction of target mRNAs susceptible to being regulated by the signature of the five miRNAs. Biological networks were created using Cytoscape software. Each network includes two types of nodes: the five individual miRNAs included in the 5-miRNA signature and their predicted target mRNAs (yellow circles), obtained from two different public databases (miRTarBase and miRecords). The number of databases included in the analysis defines the threshold regulatory interaction network (RIN). Therefore, in Rin=1, the network includes all the target mRNAs appearing in at least one database. The databases included in the RIN are identified by the color of the connecting arrows: miRTarBase and miRecords. Although many mRNAs are potential targets of miR-149-5p and miR-342-5p, the miRTarBase and miRecords versions included in this study did not reveal any experimentally validated target for the two miRNAs.

Figure 7:

FIG. 7 shows Gene Ontology (GO) terms related to the mRNAs predicted to be targets of the 5-miRNA signature. A GO analysis was conducted using "biological process" vocabulary terms. The GO identification number (GO ID), the biological process name (GO term) and the target mRNAs associated with each GO term are shown. Only GO terms with experimental evidence and a corrected p-value <0.01 were considered.

Figure 8:
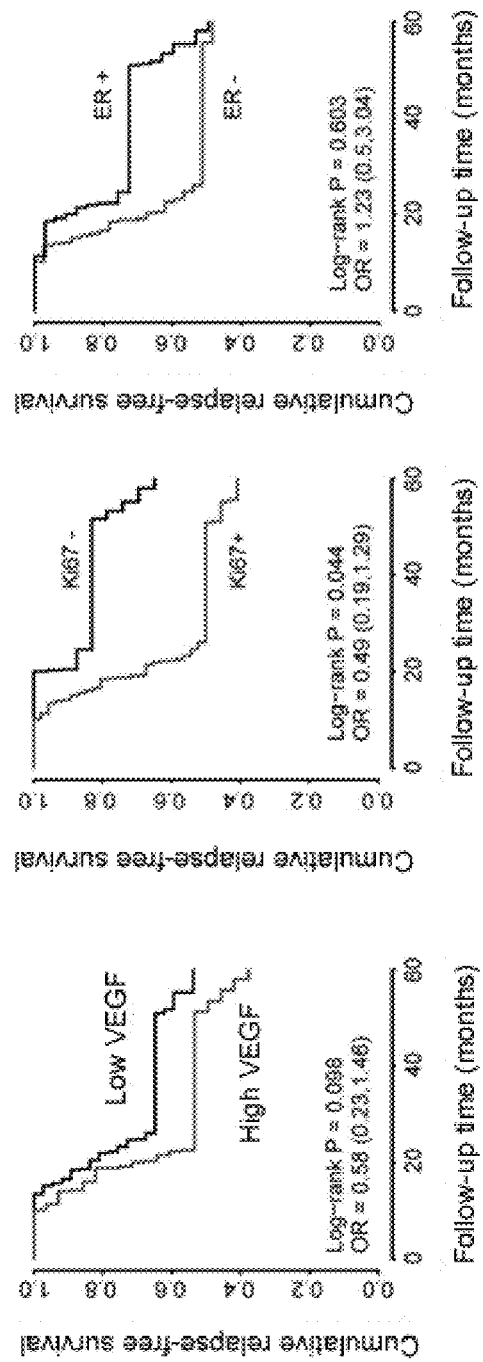

FIG. 8 shows that patients with a higher risk of relapse have breast tumors with higher proliferative capacity. The angiogenic capacity, proliferative capacity and the expression of estrogen receptors (ERs) in primary tumors was determined by means of immunohistochemistry with antibodies specific for the vascular endothelial growth factor (VEGF), Ki67 protein and ER hormone receptor, respectively. The tumors were classified according to the VEGF status (high VEGF/low VEGF, indicating high expression or low expression/lack of expression, respectively), the Ki67 status (Ki67+ or Ki67−, indicating expression or lack of expression, respectively) and the ER status (ER+ or ER−, indicating expression or lack of expression, respectively) and the cumulative RFS of the patients was calculated. The Kaplan-Meier graphs show a drop in RFS in patients with tumors with a high expression of VEGF, positive for Ki67 and negative for ER, although the differences were statistically significant only for Ki67 (Log-rank p=0.044). The 71 tumors included in this study were processed for the Ki67 and ER staining, whereas only 67 could be processed for VEGF staining.

Figure 9:
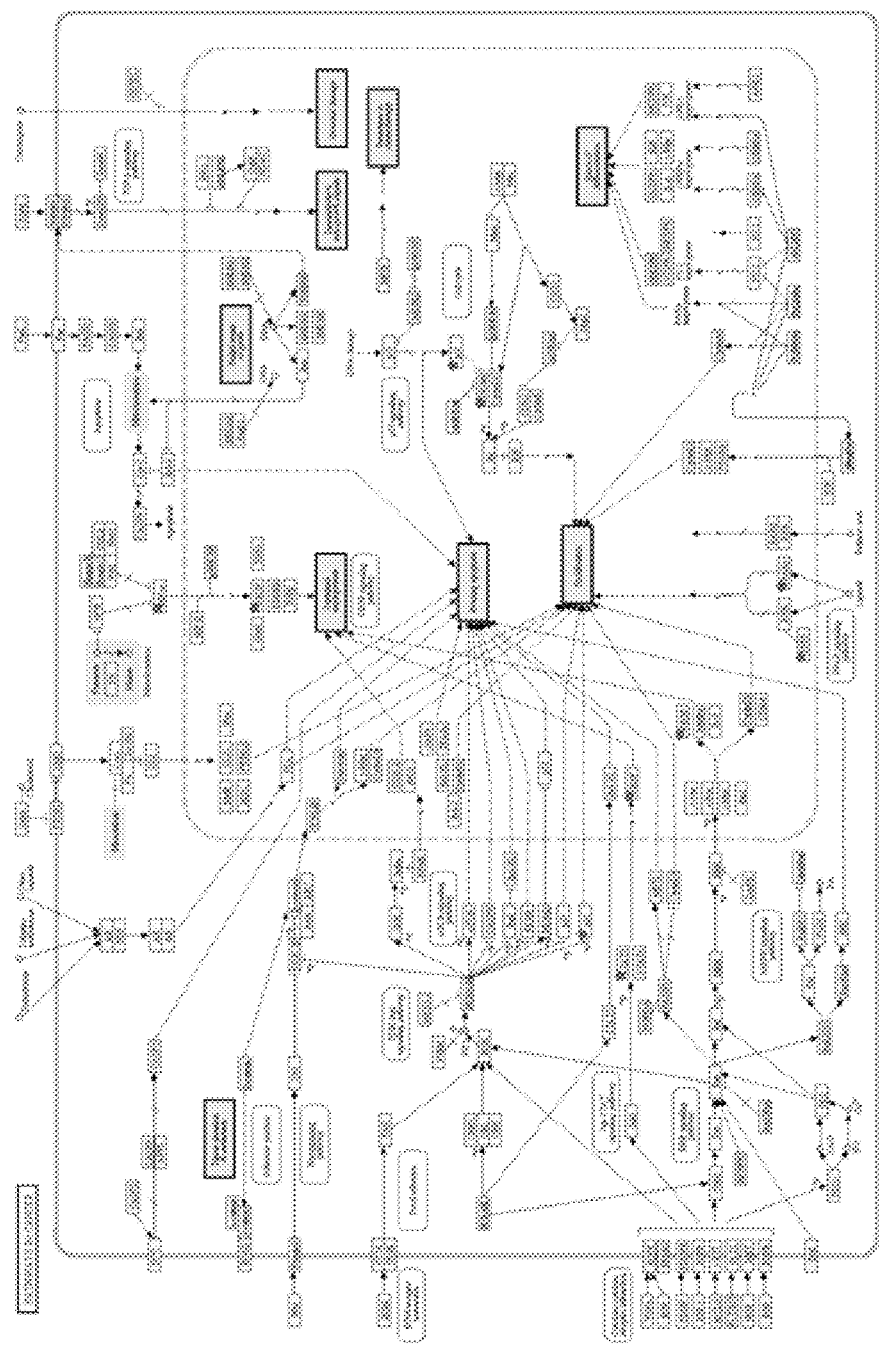

FIG. 9 shows a summary of the potential biological functions affected by the expression of the 5-miRNA signature in recurrent breast tumors (<2 years). The group of 30 target mRNAs predicted for the 5-miRNA signature (shown in FIG. 6) were integrated in the KEGG (Kyoto Encyclopedia of Genes and Genomes) server to generate a map of key proteins (indicated with stars) and the most likely pathways associated with the target mRNAs. It must be observed that an increase in target mRNAs (due to the reduced expression of the 5-miRNA signature in tumors with early recurrence) would give rise to a net increase in proliferation and angiogenesis.

DETAILED DESCRIPTION OF THE INVENTION

The detailed description discloses specific and/or preferred variants of the individual features of the invention. The present invention also contemplates as particularly preferred embodiments those embodiments that are generated by combining two or more of the specific and/or preferred variants described for two or more of the features of the present invention.

The present invention provides a method for predicting the early recurrence of breast cancer, wherein the subject suffers or has suffered from breast cancer.

According to recent studies, for women with early stage breast cancer subjected to breast conserving treatment, locoregional recurrence is still the most important prognostic factor after five disease-free years. Furthermore, after an interval of ten disease-free years, locoregional recurrence is still the only remaining independent prognostic factor. Locoregional recurrence, tumor size, the spread of cancer to the lymph nodes, young age, the presence of estrogen receptors and chemotherapy treatment are independent prognostic factors with a significant impact on the long-term result, locoregional recurrence being the most powerful factor.

The bimodal recurrence model is based on the concept of tumor latency and on the concept that metastatic homeostasis is disrupted when the tumor is removed [11, 12]. The tumor cells leave the primary site of the tumor and settle in different remote tissues where they remain in a latent state for a variable time period, either as individual cells or as micrometastases [102-104]. Most micrometastases do not actively proliferate and only a small proportion (<10%) has an angiogenic phenotype [11].

Non-angiogenic micrometastases remain dormant in the absence of an angiogenic change, and even angiogenic micrometastases cannot go beyond being avascular foci without suitable neovascularization. The dormancy therefore results from the balance between pro- and anti-angiogenic signals affecting micrometastases. Genetic changes acquired in the natural course of the disease could in turn lead to an imbalance between pro- and anti-angiogenic factors favoring neovascularization and growth of micrometastatic foci (the "angiogenic switch") [103]. The bimodal recurrence model assumes that the primary tumor contributes to homeostasis of the remote metastasis by means of releasing anti-angiogenic factors which keep angiogenic metastatic cells in a latent avascular state. Surgical removal of the tumor would do away with angiogenic repression and favor the metastatic process. Furthermore, various growth factors and cytokines released as a consequence of the wound sustained by tissue during surgery would add angiogenic stimuli, driving the metastatic process [9, 11, 13]. The inventors have described the presence of intrinsic tumor features favoring metastatic growth.

Those subjects whose recurrence is predicted in the present invention are human subjects who are suffering or have suffered from breast cancer. The terms "human subject," "subject" and "patient" are therefore used interchangeably in this specification.

As it is also used in the present specification, the expression "one or more" includes one and the individualized specification of any number that is more than one, such as two, three, four, five, six, etc. As it is used in the present specification, the expression "more than one" or "some" includes the individualized specification of any number that is more than one, such as two, three, four, five, six, etc.

Unless expressly specified otherwise, the term "comprising" is used in the context of this document to indicate that additional members besides the members of the list introduced by the term "comprising" can optionally be present. However, the term "comprising" including the possibility that additional members are not present is contemplated as a specific embodiment of the present invention, i.e., for the purposes of this embodiment "comprising" must be understood as having the meaning of "consisting of."

In the context of this specification, the term "treatment" or "treating" mean the administration of an agent for preventing, alleviating or eliminating breast cancer or one or more symptoms associated with said disease. "Treatment" also includes preventing, alleviating or eliminating the physiological sequelae of the disease. In the context of this specification, the term "treatment" or "antitumor treatment" also includes surgical removal of the tumor. In the context of this invention, the term "alleviate" is understood to mean any improvement in the treated patient's situation, i.e., subjective improvement (the feelings of or about the patient) and objective improvement (the measured parameters).

In the context of this specification, the term "miRNA signature" (or similar terms such as "signature of the five miRNAs" for example) refers to the expression profile of at least one, preferably 2, more preferably 3, even more preferably 4 and still more preferably the five miRNAs of the invention (as described in SEQ ID NOs: 1-5).

Methods for Predicting the Risk of Recurrence of Breast Cancer

The present invention is partially based on the identification of particular microRNAs in breast cancer cells and the association of these microRNAs with particular prognostic features.

MicroRNAs are single-stranded RNAs with ~22-nucleotides (about 18-25 nucleotides) negatively regulating (inhibiting) gene expression by means of inhibiting translation or cleavage of mRNA. miRNAs are therefore post-transcriptional regulators that bind to complementary sequences in target messenger RNA (mRNA) transcriptions, resulting in translation repression or target degradation and gene silencing. Most known miRNA genes are located in intergenic regions or are oriented antisense with respect to adjacent genes, so it is thought that they are transcribed as independent units. Their genes are usually transcribed by means of the RNA polymerase II, and the processed transcripts are exported from the nucleus and additionally processed by means of specific mechanisms that are well-known in the art (see, for example, He et al., Nat. Rev. Genet. July 2004; 5(7):522-31). The miRNA sequences can be accessed at http://www.mirbase.org.

In a particular aspect of the invention, understanding of the molecular details of the action of the miRNAs of the invention is not critical because the detected levels of indicator miRNAs only allow carrying out the method of the invention. It is understood that the active RNA molecule with 18-25 nucleotides can also be produced directly by chemical or biological synthesis, without having to be processed from the precursor miR.

In a normalized nomenclature system, the names are assigned to experimentally confirmed miRNAs as follows: the prefix "mir" is followed by (a hyphen and) a number, wherein said number can indicate the nomenclature order. "mir-" in lower case refers to pre-miRNA, whereas "miR-" in upper case refers to the mature form. miRNAs with virtually identical sequences, except for one or two nucleotides, are indicated in additional lower case letters, for example miR-10a-5p. Pre-miRNAs leading to 100% identical mature miRNAs but located in different areas in the genome are indicated with an additional numerical suffix separated by a hyphen. The original species can be designated with a three-letter prefix, for example, miR-10a-5p is a human (*Homo sapiens*) miRNA. Since in the context of this document all individualized miRNAs are human miRNAs, the prefix "hsa-" is omitted sometimes. When two microRNAs come from opposite arms of the same pre-miRNA, they are denoted with a -3p or -5p suffix, such as miR-10a-5p, for example. When relative expression levels are known, an asterisk after the name indicates a miRNA expressed at low levels with respect to the miRNA in the opposite arm of a hairpin.

As they are used in the present document interchangeably, a "miRNA gene product," "miRNA," "microRNA" or "miR" refers to the processed or unprocessed RNA transcribed from a miR gene. Since the miR gene products are not translated into proteins, the expression "miR gene products" does not include proteins. Furthermore, the expression "expression levels of miRNA" refers to the levels of miRNA, therefore without including proteins.

Recurrence of the tumor or recurrence of breast cancer can be defined as the reappearance of the tumor (or of the cancer) after treatment. Recurrence can be local (in the same breast or in the mastectomy scar) or in a remote area. In the context of the present invention, recurrence is preferably in a remote area (metastasis).

The present inventors have investigated the association between the miRNA profile and the recurrence of breast cancer in patients who are suffering or have suffered from breast cancer, preferably in patients who have been treated to fight against said breast cancer. In a particular embodiment, the patients have been subjected to surgery for removing the tumor. In a preferred embodiment, the tumor that is removed during surgery is a primary tumor.

In a first aspect, the invention provides a method for estimating or predicting the risk of recurrence of breast cancer. Said method comprises detecting the levels of one or more miRNAs in particular in a sample from a human subject. Illustrative, non-limiting examples of said samples include different types of tissue samples and biological fluid samples, such as blood, serum, plasma, cerebrospinal fluid, peritoneal fluid, or feces. Said samples are preferably tissue samples, and said tissue samples most preferably come from tissue of the tumor of the individual whose recurrence is to be predicted, and it can come from biopsies, preferably from surgical resection.

The levels of one or more miRNAs in particular measured in the method of the present invention are preferably selected from the following miRNAs: SEQ ID NO: 1 (miR-149-5p); SEQ ID NO: 2 (miR-10a-5p); SEQ ID NO: 3 (miR-20b-5p); SEQ ID NO: 4 (miR-30a-3p); SEQ ID NO: 5 (miR-342-5p).

TABLE 1 miRNA sequences

| MicroRNA | SEQ ID NO | Accession Number (miRBase) | Mature Sequence |
| --- | --- | --- | --- |
| hsa-miR-149-5p | 1 | MIMAT0000450 | ucuggcuccgug ucuucacuccc |
| hsa-miR-10a-5p | 2 | MIMAT0000253 | uacccuguagau ccgaauuugug |
| hsa-miR-20b-5p | 3 | MIMAT0001413 | caaagugcucau agugcagguag |
| hsa-miR-30a-3p | 4 | MIMAT0000088 | cuuucagucgga uguuugcagc |
| hsa-miR-342-5p | 5 | MIMAT0004694 | aggggugcuauc ugugauuga |

Figure 2:
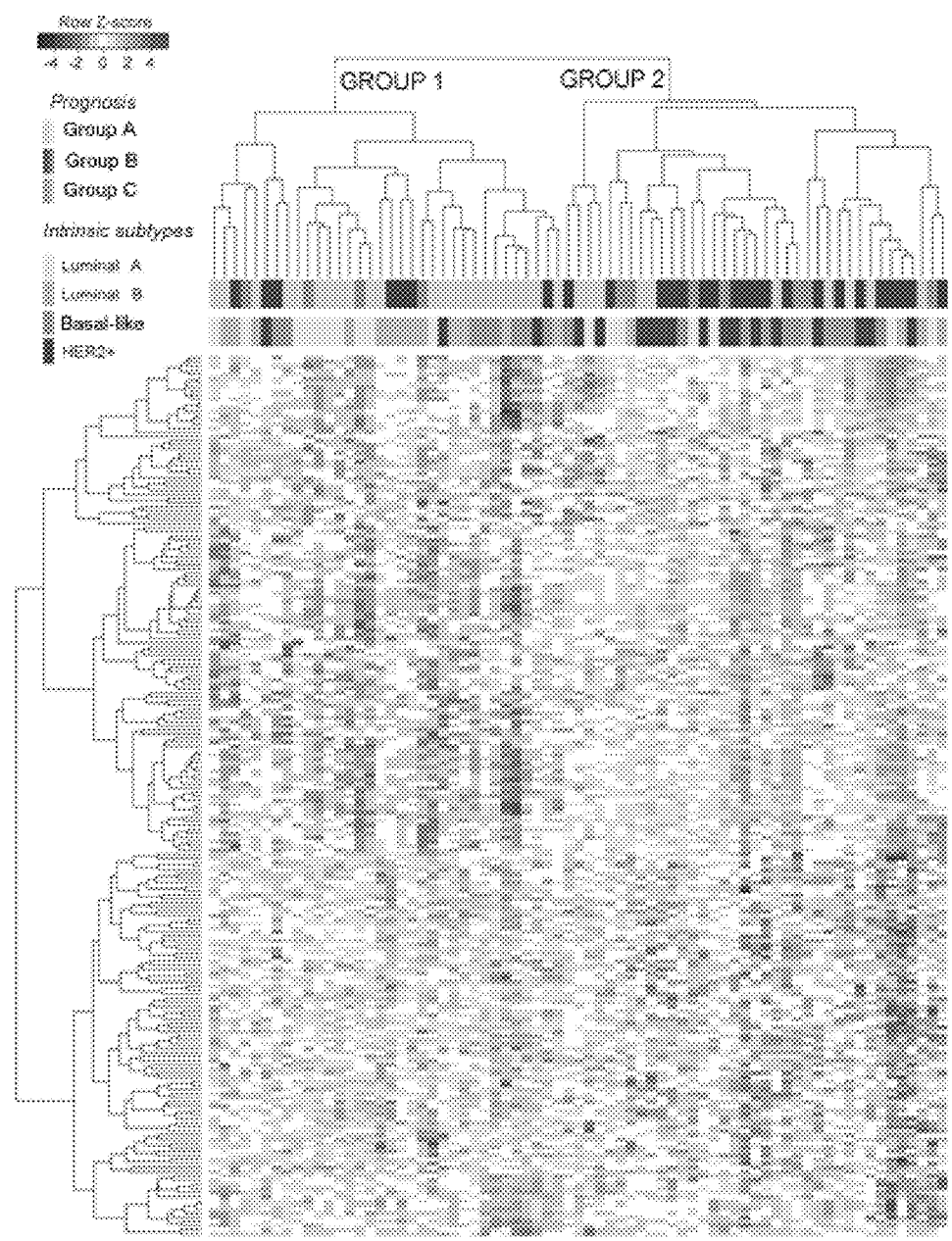
FIG. 2 shows expression profiles of the miRNAs in primary tumors of patients with different prognoses. Total RNA was obtained from 71 breast tumors, converted into cDNA and hybridized to the Affymetrix 2.0 miRNA microarray chip. After normalization, the difference in the miRNA expression data was analyzed using an unsupervised hierarchical clustering algorithm. The colored bars in the upper part of the heat map refer to the prognosis group and intrinsic subtype of each tumor. Group A includes the tumors in patients who are disease free for ≥60 months after surgery, group B includes the tumors in patients with early recurrence (≤24 months) and group C includes the tumors in patients with late recurrence (50 to 60 months after surgery). The tumors are grouped into two main groups (cluster 1 and cluster 2 in the figure), showing expression profiles that are opposite and strongly associated with the prognosis groups.

The inventors have provided evidence that these miRNAs are indicators of the risk of recurrence of the tumor in a subject (see, for example, FIG. 2).

The levels of these particular miRNAs are compared with the levels of those same miRNAs in a reference sample or with a control value. In the context of the present invention, "reference sample" is understood as the reference sample that is used for determining the variation in the levels of the miRNAs of the present invention. In one embodiment, the reference value is obtained from the signal provided using a tissue sample obtained from an individual who has not presented a recurrence. Samples are preferably taken from the same tissue from several individuals who have not presented a recurrence and are combined such that the reference value reflects the average value of said molecules in the population of subjects who do not present recurrence. The "reference value" can be defined as the level of a miRNA of the invention in the reference sample. In one embodiment, the reference value indicative of non-recurrence for each specific miRNA must be known before carrying out the method of the present invention.

In another embodiment, the reference value is obtained from the signal provided by a nucleic acid the levels of which remain stable regardless of variable factors such as age, cell type, disease (for example recurrence/non-recurrence of the tumor), sex, the physiological state, or the response to external conditions, or the like.

Figure 1:
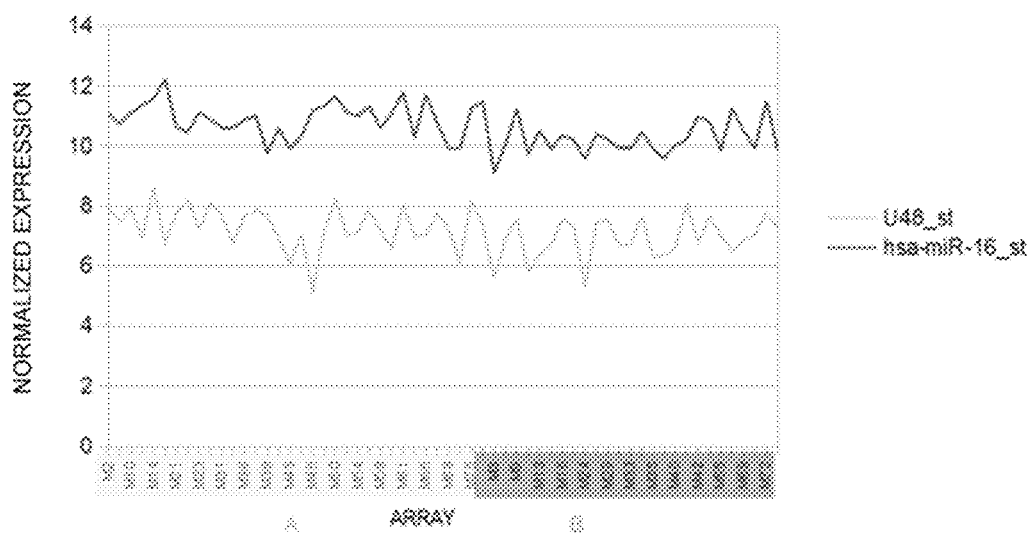
FIG. 1 shows the stability of the expression levels of RNU48 and miR-16-5p in samples of recurrent tumors (B) and non-recurrent tumors (A). For this calculation, after the reading of each microarray according to Example 2 of the present invention, all the signals are normalized taking into account all the probes of the microarray by means of a standard mathematical process, i.e., the RMA (Robust Multi-Array Average, citation: ˆIrizarry, R A; Hobbs, B; Collin, F; Beazer-Barclay, Y D; Antonellis, K J; Scherf, U.

For example, the reference value can be obtained from the signal provided by RNU6B (SEQ ID No: 6), and/or RNU48 (SEQ ID No: 7), and/or miR-16-5p (SEQ ID No: 8). The reference value can preferably be obtained from the signal provided by RNU48, and/or miR-16-5p. FIG. 1 shows the stability of the expression levels of RNU48 and miR-16-5p in samples of recurrent tumors (B) and non-recurrent tumors (A). This graph only shows the expression values (after RMA normalization) of RNU48 and miR16, demonstrating that their expression is stable.

The reference sample is preferably from the same tissue and/or obtained by means of the same method as the sample from which the risk of recurrence of the tumor in the subject is to be predicted.

Therefore, by means of the method of the invention it can be predicted if an individual patient exhibits (i) a high risk of recurrence of the tumor, or (ii) a low risk of recurrence of the tumor. The inventors have demonstrated that when the risk of recurrence is high, the expression levels of one or more miRNAs, preferably of all the miRNAs as defined in SEQ ID NOs: 1, 2, 3, 4 and 5, have dropped compared with a reference value.

The amount of target miRNA, normalized to an endogenous reference and with respect to a control sample, is indicative of the risk of recurrence of the tumor. For example, if the expression level of one or several (preferably all) of the miRNAs of the present invention (the signature of the 5-miRNAs) in a sample of a (preferably primary) tumor from a subject is lower than the expression level of one (or several) of the control nucleic acid(s) from that same subject (in that same tumor or in adjacent tissues, or tissues located away from the tumor), then the risk of recurrence as defined in the present invention is high. The expression levels of one or several (preferably all) of the miRNAs of the present invention (the signature of the 5-miRNAs) in a sample of a (preferably primary) tumor are considered to be lower than the expression level of one (or several) of the control nucleic acid(s) from that same subject if the ratio of the value of the normalized expression levels of the one or several miRNAs and the normalized expression levels of one (or several) of the control nucleic acid(s) is less than 1, preferably less than 0.95, more preferably less than 0.9, such as less than 0.85 for example, such as less than 0.75 for example, such as less than 0.7 for example, such as less than 0.5 for example, such as less than 0.3 for example, such as 0.1 for example, such as less than 0.05 for example, such as less than 0.01 for example.

For example, if the ratio of the expression levels of one or several (preferably all) of the miRNAs of the present invention (the signature of the 5-miRNAs) in a sample of a tumor (Rx) and the normalized expression levels of one (or several) of the control nucleic acid(s) (Rc) is less than 1 (for example 0.9, or 0.85, or 0.75, or 0.7, or 0.65, or 0.6, or 0.5, or 0.4, or 0.3, or 0.2, or 0.1, or 0.05, 0.01, etc.), the risk of recurrence as defined in the present invention is high.

High risk of recurrence: Rx/Rc≤1

The risk of recurrence according to the present invention can be defined as the probability of the tumor reappearing after a given period of time after antitumor treatment, preferably after surgical removal of the tumor, preferably a primary tumor. For example, the tumor can reappear from 3 months to 10 years after antitumor treatment, preferably from 3 months to 5 years after antitumor treatment, more preferably from 1 year to 4 years after antitumor treatment, even more preferably from 1.5 years to 2 years after antitumor treatment. For example, the tumor can reappear 3 months after antitumor treatment. For example, the tumor can reappear 6 months after antitumor treatment. For example, the tumor can reappear 1 year after antitumor treatment. For example, the tumor can reappear 2 years after antitumor treatment. For example, the tumor can reappear from 0 to 2 years after antitumor treatment. For example, the tumor can reappear 5 years after antitumor treatment. Preferably, the risk of recurrence according to the present invention can be defined as the probability of the tumor reappearing from 1 to 2 years after antitumor treatment (preferably surgery). The risk of recurrence defined as the probability of the tumor reappearing from 0 to 2 years after antitumor treatment (preferably surgery) can also be referred to as "risk of early recurrence" throughout the present specification.

Therefore, the risk of recurrence according to the present invention preferably refers to the risk of the occurrence of metastasis in a period of not more than two years after antitumor treatment (preferably surgery).

A high (or interchangeably elevated) risk of recurrence can be defined as a more than 50% probability of the tumor reappearing in said subject. Preferably, a high risk of recurrence is defined as a more than 55% probability of the tumor reappearing, such as, for example, a 60% probability of the tumor reappearing. Preferably, a high risk of recurrence is defined as a more than 63% probability of the tumor reappearing, such as, for example, a more than 70%, 75%, 80%, 85% or 90% probability. Preferably, a high risk of recurrence is defined as a more than 99% probability of the tumor reappearing.

A low risk of recurrence can be defined as a less than 50% probability of the tumor reappearing in said subject. Preferably, a low risk of recurrence is defined as a less than 45% probability of the tumor reappearing, such as, for example, a 40% probability of the tumor reappearing. Preferably, a low risk of recurrence is defined as a less than 37% probability of the tumor reappearing, such as, for example, a less than 30%, 25%, 20%, 15%, 10% or 1% probability. Preferably, a low risk of recurrence is defined as a less than 1% probability of the tumor reappearing Therefore, in one embodiment of the present invention, a high risk of recurrence can be defined as a more than 50% probability, and/or a more than 55% probability and/or a more than 60% probability and/or a more than 63% probability of the tumor reappearing, such as, for example, a more than 70%, 75%, 80%, 85%, 90% probability, or a more than 99% probability of the tumor reappearing in the subject in question from 3 months to 10 years after antitumor treatment, preferably from 3 months to 5 years after antitumor treatment, more preferably from 1 year to 5 years after antitumor treatment, even more preferably from 1 to 2 years after antitumor treatment (preferably surgery).

Therefore, in another embodiment of the present invention a high risk of recurrence can be defined as a more than 50% probability, and/or a more than 55% probability and/or a more than 60% probability and/or a more than 63% probability of the tumor reappearing, such as, for example, a more than 70%, 75%, 80%, 85%, 90% probability, or a more than 99% probability of the tumor reappearing in the subject in question from 1 to 2 years after antitumor treatment.

Therefore, in another embodiment of the present invention a high risk of recurrence can be defined as a more than 60% probability of the tumor reappearing in the subject in question from 1 to 2 years after surgery for removing the tumor.

Therefore, in another embodiment of the present invention a high risk of recurrence can be defined as a more than 63% probability of the tumor reappearing in the subject in question from 1 to 2 years after surgery for removing the tumor.

Therefore, in another embodiment of the present invention a high risk of recurrence can be defined as a more than 70% probability of the tumor reappearing in the subject in question from 1 to 2 years after surgery for removing the tumor.

Therefore, in another embodiment of the present invention a high risk of recurrence can be defined as a more than 85% probability of the tumor reappearing in the subject in question from 1 to 2 years after surgery for removing the tumor.

The probability of recurrence increases with the number of miRNAs (selected from the following miRNAs: SEQ ID NO: 1 (miR-149-5p); SEQ ID NO: 2 (miR-10a-5p); SEQ ID NO: 3 (miR-20b-5p); SEQ ID NO: 4 (miR-30a-3p); SEQ ID NO: 5 (miR-342-5p), the levels of which are reduced in the sample of the tumor with respect to the control, as described above. For example, if a subject has reduced levels of a single miRNA (selected from the following miRNAs: SEQ ID NO: 1 (miR-149-5p); SEQ ID NO: 2 (miR-10a-5p); SEQ ID NO: 3 (miR-20b-5p); SEQ ID NO: 4 (miR-30a-3p); SEQ ID NO: 5 (miR-342-5p) with respect to the control, the risk of recurrence can be about 55%-65%, preferably about 62%.

For example, if a subject has reduced levels of at least two miRNAs (selected from the following miRNAs: SEQ ID NO: 1 (miR-149-5p); SEQ ID NO: 2 (miR-10a-5p); SEQ ID NO: 3 (miR-20b-5p); SEQ ID NO: 4 (miR-30a-3p); SEQ ID NO: 5 (miR-342-5p) with respect to the control, the risk of recurrence can be about 60%-65%, preferably about 63%.

For example, if a subject has reduced levels of at least three miRNAs (selected from the following miRNAs: SEQ ID NO: 1 (miR-149-5p); SEQ ID NO: 2 (miR-10a-5p); SEQ ID NO: 3 (miR-20b-5p); SEQ ID NO: 4 (miR-30a-3p); SEQ ID NO: 5 (miR-342-5p) with respect to the control, the risk of recurrence can be about 65%-72%, preferably about 71%.

For example, if a subject has reduced levels of at least four miRNAs (selected from the following miRNAs: SEQ ID NO: 1 (miR-149-5p); SEQ ID NO: 2 (miR-10a-5p); SEQ ID NO: 3 (miR-20b-5p); SEQ ID NO: 4 (miR-30a-3p); SEQ ID NO: 5 (miR-342-5p) with respect to the control, the risk of recurrence can be about 70%-75%, preferably about 72%.

For example, if a subject has reduced levels of the five miRNAs (5-miRNA signature) (selected from the following miRNAs: SEQ ID NO: 1 (miR-149-5p); SEQ ID NO: 2 (miR-10a-5p); SEQ ID NO: 3 (miR-20b-5p); SEQ ID NO: 4 (miR-30a-3p); SEQ ID NO: 5 (miR-342-5p) with respect to the control, the risk of recurrence can be about 85%-90%, preferably about 87%.

It is preferable for the subject in whom recurrence is to be predicted to have experienced surgery on the tumor, i.e., surgical resection of the cancer before applying the method of the invention. Surgical options include but are not limited to (a) partial mastectomy (only part of the breast is removed) b) mastectomy (the entire breast is removed and involves removing all breast tissue, and sometimes adjacent tissues as well). Therefore, the levels of at least one, preferably two, more preferably three, even more preferably four and still more preferably five miRNAs of the invention are determined from the primary tumor obtained by surgery. Furthermore, preferably the levels of RNA used as a reference sample, as indicated above, are preferably obtained from tissue from the same patient. For example, they can be obtained from the same tumor or from healthy adjacent tissue.

Use of other treatments such as radiation or chemotherapy, together with surgery, is not excluded. In the context of the present invention, chemotherapy is understood as cancer treatment with an antineoplastic drug or with a combination of said drugs. Without seeking to be linked with any particular theory, it is understood that chemotherapy normally acts by killing rapidly dividing cells, which is one of the main properties of most cancer cells.

It is possible that at the time of taking the sample from the human subject, the human subject (i) may be undergoing chemotherapy treatment or (ii) may not be undergoing chemotherapy treatment. The following sequence is particularly preferred: (a) patients with breast cancer experiencing surgery on the (preferably primary) breast tumor, (b) during surgery, a sample of the tumor is taken out for miRNA analysis, (c) (optional) the patients are treated by means of chemotherapy. The sample of the tumor is preferably a recent sample of the tumor, but it can also be a non-recent sample of the tumor, for example, such as a sample of a tumor stored in paraffin for example.

Isolation of the sample from the living subject as such is not part of the invention. Surgery on a living human body as such is not part of the invention. What is part of the invention is the in vitro method for determining the expression level of the miRNAs of the invention in a sample that has been obtained by means of steps (a) and (b). The method for predicting recurrence of the tumor according to the present invention is therefore preferably an in vitro method.

In practice, step (b) usually comprises (b1) extracting (total) RNA or (total) miRNA from the sample of the tumor, and the methods suitable for this purpose are not particularly limited. This also usually comprises step (b2), i.e., detecting the levels of the miRNAs of interest in the RNAs extracted in (b1). Suitable exemplary and non-limiting methods are provided in the materials and methods section.

The method of the present invention can be applied to samples from individuals of any age. For example, the method of the present invention can be applied to samples from individuals less than 50 years old. For example, the method of the present invention can be applied to samples from individuals more than 50 years old. Preferably, the method of the present invention is applied in women.

In the invention, the method of determining the result, i.e., the expression level of the miRNA, does not require being limited in a particular manner and can be selected from a gene profiling method, such as a microarray, and/or a method comprising PCR, such as real-time PCR; and/or Northern blot.

A microarray is an array on a solid substrate (usually a glass slide or a silicon thin-film cell) that assays large amounts of biological material, in this case, a large amount of different miRNAs or, preferably, their reverse DNA transcripts, which are detectable by means of specific probes immobilized on the solid substrate.

Northern blot involves the use of electrophoresis to separate RNA samples by size and subsequent detection with a probe that is complementary to (part of) the target sequence of the RNA of interest.

Real-time quantitative PCR (RQ-PCR) is a technique for quantifying the sensitive and reproducible gene expression that can be used in a particular manner for expression of the miRNA profile in cells and tissues. Any method can be used to evaluate the results of the RT-PCR, and the $\Delta\Delta C_t$ method may be preferred. The $\Delta\Delta C_t$ method is described in detail in Livak et al. (Methods 2001, 25:402-408) ($C_t$=cycle threshold values). When the present invention is carried out to practice, the $\Delta\Delta C_t$ method as described by Livak et al. (Methods 2001, 25:402-408) should preferably be used. The $\Delta\Delta C_t$ method will involve a "control sample" and a "sample from the subject."

The "sample from the subject" is a sample from the subject to be analyzed. One target gene (the miRNA of interest in the present invention) and an endogenous control gene (as described below) are included for each sample for PCR amplification from aliquots (usually serial dilutions). Several replicas of each diluted concentration are normally used to calculate amplification efficiency. PCR amplification efficiency can be defined as the percentage of amplification (from 0 to 1). During the qPCR reaction, software usually measures the number of cycles of each sample in which fluorescence crosses an arbitrary line (PCR amplification indicator), i.e., the threshold. This crossing point is the $C_t$ value. More diluted samples will cross at later $C_t$ values.

In the method of the present invention, it is possible to normalize expression of the miRNA in relation to an endogenous control. The endogenous control is preferably the endogenous expression (i.e., in the same individual) of another nucleic acid, preferably an RNA, such as any one selected from mRNA, miRNA, nucleolar RNA, rRNA and the like. It is largely preferred for said RNA to be known as being expressed in a stable manner. Stable expression means any expression known as being expressed independently of variable factors such as age, cell type, disease, sex, physiological state, or response to external conditions, or the like. In a particular embodiment, this nucleic acid can be chosen from small nucleolar RNAs and is preferably RNU6b and/or RNU48. Other nucleolar RNAs such as RNU44, RNU48, RNU24, RNU43, RNU6B, RNU19, and Z30, as well as gene miRNA, can also be used for normalization. RNU44 and RNU48 can be particularly useful. Preferably, miR-16 can additionally or optionally be used.

The endogenous expression of RNU6B, and/or RNU48, and/or miR-16-5p is preferably used for normalizing expression of the miRNA(s). The endogenous expression of miR-16-5p and RNU48 is preferably used.

All the miRNA nucleotide sequences can be accessed online at the miRBase, which is the main online depository of all microRNA sequences and annotations (Kozormara et al., Nucl. Acids Res. (2011) 39 (suppl 1)). The nucleotide sequences of other human RNAs, such as small nucleolar RNAs, can be found online at http://www.ncbi.nlm.nih.gov/

(GRCh37 assembly (GCA_000001405.6) from the Genome Reference Consortium). Additional molecules suitable for normalization are described in Davoren et al., BMC Mol Biol. 2008; 9: 76, and can be used in the method of the invention.

```
RNU6B NR_002752 (SEQ ID NO: 6) sequence:
GUGCUCGCUUCGGCAGCACAUAUACUAAAAUUGGAACGAUACAGAGAAG
AUUAGCAUGGCCCCUGCGCAAGGAUGACACGCAAAUUCGUGAAGCGUUC
CAUAUUUUU RNU48 NR_002745 (SEQ ID NO: 7) sequence:
AGUGAUGAUGACCCCAGGUAACUCUGAGUGUGUCGCUGAUGCCAUCACC
GCAGCGCUCUGACC miR-16-5p MIMAT0000069 (SEQ ID NO: 8) sequence:
UAGCAGCACGUAAAUAUUGGCG
```

It is also possible to use more than one different RNA for normalization, such as two or more, three or more and/or up to five different RNAs. Expression of the miRNA is preferably normalized in relation to endogenous expression (i.e., in the same individual). The endogenous expression of miR-16-5p and RNU48 is preferably used.

In any case, the reference value is obtained by normalization with respect to the same nucleic acid as the value from which the response of the patient is to be predicted. For merely illustrative purposes, if the reference value is obtained by normalization of the expression of one/several of the specific miRNA(s) of the invention for the expression of miR-16-5p and/or RNU48, then in the patient in whom the response is to be predicted, the expression value is also obtained by normalization of the expression of one/several of the specific miRNA(s) of the invention for the expression of miR-16-5p and/or RNU48.

To quantify the miRNA gene expression, the $C_t$ of a nucleic acid can be from the miRNA of the gene of interest can be divided by the $C_t$ of the nucleic acid from the endogenous control in the same sample for normalizing the variation in the amount and quality of the RNA among different samples and obtaining the relative expression (with respect to the endogenous control) of each of the "sample from the subject" and the "control sample". Optionally, this is done in duplicate, triplicate, quadruplicate and so on, respectively. Optionally, a $\Delta C_t$ control value can be obtained in a suitable manner by calculating the average $\Delta C_t$ values obtained from samples from a control group of several individuals with which the values of the "sample from the subject" are to be compared.

Preferably, to quantify the miRNA gene expression, the normalized expression value of one or more miRNAs of the present invention is calculated as follows. This mode of calculation also applies to cases in which the normalizing nucleic acids are different, or when there is one or several normalizing nucleic acid(s).

First it is necessary to calculate the amplification efficiency (e) and the cycle threshold (Ct) for each sample and each miR (including normalizing miRs). Then the mean efficiency (E) of a miR x is defined as the average value of all the efficiencies for that miR.

$$E=(e1+e2+e3 \ldots en)/n,$$

where n is the number of patients.

The expression value (R) of a given miR (x) for a sample (n) is obtained from the following formula:

$$Rxn=(1+Ex)^\wedge-Ctx,$$

where Ctx is the cycle threshold of miR x for the sample n. For example, for the normalizing nucleic acid RNU6b:

$$R6bn=(1+E6b)^\wedge-Ct6b,$$

where E6b is the amplification efficiency of RNU6b and Ct6b is its cycle threshold for the sample n.

For example, for the normalizing nucleic acid miR-16, it would be:

$$R16n=(1+E16)^\wedge-Ct16,$$

where E16 is the amplification efficiency of miR x and Ct16 is its cycle threshold for the sample n.

Finally the normalized expression value for miR x in the sample n is calculated as follows:

$$Rn=Rxn/(Rn1+Rn2)$$

where the denominator (Rn1+Rn2 in this case) is the sum of the expression values (R) of one or more control nucleotides ((R6bn+R16n) in this case).

This normalized expression value is what is preferably used. Calculations for the efficiency and cycle threshold values for each sample are preferably performed as indicated in Zhao and Fernald. J. Comput. Biol. 2005 October; 12(8): 1045-62.

Any sequence that the person skilled in the art is able to identify can be used as primers for the PCR amplification. Primers exhibit a part that is complementary to the sequence of each miRNA to be amplified. For example, probes (primers) available on the market, such as, for example, Applied Biosystems TaqMan® probes, can be used. The probes can be labeled (for example with a fluorophore) to make detection easier.

Sequences that can be used as primers for amplifying the miRNAs of the invention by RT-PCR are described in detail below only by way of example:

```
For amplifying miR-149-5p:
                        (SEQ ID NO: 9)
5-GGGAGTGAAGACACGGAGCCAGA-3

For amplifying miR-10a-5p:
                        (SEQ ID NO: 10)
5-CACAAATTCGGATCTACAGGGTA-3

For amplifying miR-20b-5p:
                        (SEQ ID NO: 11)
5-CTACCTGCACTATGAGCACTTTG-3

For amplifying miR-30a-3p:
                        (SEQ ID NO: 12)
5-GCTGCAAACATCCGACTGAAAG-3

For amplifying miR-342-5p:
                        (SEQ ID NO: 13)
5-TCAATCACAGATAGCACCCCT-3

For amplifying RNU6B:
                        (SEQ ID NO: 14)
5-AAAAATATGGAACGCTTCACG-3

For amplifying RNU48:
                        (SEQ ID NO: 15)
5-GGTCAGAGCGCTGCGGTGATG-3

For amplifying miR-16-5p:
                        (SEQ ID NO: 16)
5-CGCCAATATTTACGTGCTGCTA-3
```

In the method of the invention, one or more miRNA(s) can be used as a negative control. A non-human origin is mainly preferred for the miRNAs of the negative control.

It is also possible to isolate the miRNAs of the invention by means of any known method suitable for said purposes.

In the present invention, regardless of the method used for quantifying the miRNAs (or for quantifying the control samples) the "sample from the subject" is compared with the "control sample" (or the average control samples, as defined above). The value of the ratio of the expression values of both samples (sample from the subject/control sample) indicates the risk of recurrence, as described above.

The method of the present invention can further entail a step of providing a result in the form of data and/or information and saving that result in a support suitable for containing or saving data and/or information.

Method for Classifying a Human Subject Suffering from Breast Cancer into One of Two Groups In a second aspect, the invention also provides a method for classifying a human subject suffering from breast cancer into one of two groups. Unless otherwise implicitly or explicitly specified, the details of the invention as described above are also applied to the second aspect of the invention. Group 1 comprises the subjects that can be identified by means of the method of the invention as described in detail above exhibiting a high risk of suffering from a recurrence of the tumor; and group 2 represents the remaining subjects.

The method according to this second aspect of the invention can further entail a step of providing a result in the form of data and/or information and saving that result in a support suitable for containing or saving data and/or information.

Method for Predicting the Survival of a Subject with Breast Cancer

A third aspect of the present invention provides a method for predicting the survival of a subject who is suffering or has suffered from breast cancer.

The cancer patient survival is expressed in a suitable manner generally by means of Kaplan-Meier curves, which were named after Edward L. Kaplan and Paul Meier, who first discovered such curves (Kaplan, Meier: Amer. Statist. Assn. 53:457-481). The Kaplan-Meier estimator is also known as the product limit estimator. It serves for estimating the survival function from lifetime data. A graphical representation of the Kaplan-Meier estimate of the survival function is a series of horizontal steps having a decreasing magnitude which, when a large enough sample is taken, approaches the true survival function of this population. The value of the survival function between different successive sampled observations is assumed to be constant. The significance of the statistical differences can be estimated using, for example, a type of range test methods for censored survival data (log-rank methods and the Tarone-Ware and Peto-Peto tests).

In the statistic on which the present invention is based, breast cancer patients are grouped in categories, for example, those with a specific expression profile such as the expression profile of at least one miRNA in particular (and preferably the five miRNAs of the present invention) and those without said profile. With respect to the present invention, the Kaplan-Meier estimator can be used for measuring the fraction of living patients without recurrence of the tumor (relapse-free survival, defined as the period of time elapsing from surgery until recurrence of the tumor) throughout a certain amount of time after being subjected to surgery for removing the tumor (relapse-free survival, defined as the period of time elapsing from surgery until recurrence of the tumor).

A fourth aspect of the present invention provides a kit comprising at least one or more oligonucleotides capable of hybridizing with any one of two or more, and preferably all of the miRNAs (or with their respective cDNAs, in the case of amplification by RT-qPCR). The person skilled in the art can design these oligonucleotides. By way of example, oligonucleotide sequences that can be used for amplifying the miRNAs of the present invention (which are defined as SEQ ID NOs: 1 to 5) are included. Table 2 provides the particular embodiments of the sequences of said oligonucleotides described above.

Whenever reference is made to hybridization of the oligonucleotide(s), said oligonucleotide(s) is/are preferably capable of hybridizing in stringent conditions.

Stringency is a term used in hybridization experiments. Stringency reflects the degree of complementarity between the oligonucleotide and the nucleic acid (which in this case is the nucleic acid of the miRNA to be detected), the one of greater stringency, the highest percentage of identity between the probe and the nucleic acid bound to the filter. The person skilled in the art knows that the temperature and saline concentrations have a direct effect on the results that are obtained. The results of hybridization are acknowledged as being related to the number of degrees below the $T_m$ (melting temperature) of the DNA on which the experiment is carried out. Stringent conditions are often defined as a wash with 0.1×SSC (saline sodium citrate (SSC) buffer solution at 65° C. (SSC is usually provided as a 20× stock solution, containing 3 M sodium chloride and 300 mM trisodium citrate (adjusted to pH 7.0 with HCl)).

The kit is based on the predictive power of the method of the present invention.

As mentioned above, the indicator reference value for the low risk of recurrence of each specific miRNA can be determined before carrying out the method of the present invention, and can also be determined while carrying out the method of the present invention, by calculating the expression levels of one or more nucleic acid(s) the levels of which remain stable regardless of variable factors such as age, cell type, disease (for example recurrence/non-recurrence of the tumor), sex, physiological state, or response to external conditions or the like, and by comparing the expression levels of one or more miRNA(s) of the signature of the five miRNAs with the expression levels of the control sample or reference value. If the expression levels of one or more miRNA(s) of the signature of the five miRNAs are lower than the levels of the control sample or reference value, then the risk of recurrence as described in the present invention is high.

In the particular case of the kit, the indicator reference value for the low risk of recurrence (and/or an indicator reference value for the high risk of recurrence) can alternatively be provided with the kit.

TABLE 2

Examples of oligonucleotide sequences

| Oligonucleotide sequence | SEQ ID NO | SEQ ID NO for amplification |
|---|---|---|
| 5-GGGAGTGAAGACACGGAGCCAGA-3 | 9 | 1 |
| 5-CACAAATTCGGATCTACAGGGTA-3 | 10 | 2 |
| 5-CTACCTGCACTATGAGCACTTTG-3 | 11 | 3 |
| 5-GCTGCAAACATCCGACTGAAAG-3 | 12 | 4 |
| 5-TCAATCACAGATAGCACCCCT-3 | 13 | 5 |
| 5-AAAAATATGGAACGCTTCACG-3 | 14 | 6 |
| 5-GGTCAGAGCGCTGCGGTGATG-3 | 15 | 7 |
| 5-CGCCAATATTTACGTGCTGCTA-3 | 16 | 8 |

In particular embodiments, the kit is selected from (a) a kit suitable for PCR, (b) a kit suitable for Northern blot, and (c) a kit suitable for microarray analyses. Any two or more of these embodiments can be combined such that the kit can comprise both (a) and (c), for example.

In the case of (a), a kit suitable for PCR, this PCR is usually real-time quantitative PCR (RQ-PCR or RT-qPCR), a technique for quantifying sensitive and reproducible gene expression.

In this case it is desirable for the kit to additionally comprise a polyT oligonucleotide primer in addition to the oligonucleotide(s) of the kit (see Table 2 for an example of said primers). The polyT oligonucleotide primer can be used together with the oligonucleotide(s) of the invention for PCR priming, after polyadenylation of the miRNAs isolated by means of the methods known by the skilled person, such as using the poly(A) polymerase and ATP. These reagents can optionally be comprised in the kit.

Northern blot involves the use of electrophoresis to separate RNA samples by size and subsequent detection with one or more oligonucleotides (hybridization probe) complementary to (part of) the target sequence of the RNA of interest.

It is also possible for the oligonucleotide(s) to be immobilized in spots on a (preferably solid) surface. In one of its embodiments, the kit comprises a microarray. An RNA microarray is an array on a solid substrate (usually a glass slide or a silicon thin-film cell) that assays large amounts of different RNAs (miRNAs in this case) which are detectable by means of specific probes immobilized in spots on a solid substrate. Each spot contains a specific nucleic acid sequence, usually a DNA sequence, as probes (or indicators). Although the number of spots is not limited in any way, there is a preferred embodiment in which the microarray is customized for the methods of the invention. In one embodiment, said customized array comprises fifty spots or fewer, such as thirty spots or fewer, including twenty spots or fewer.

Preferably, the kit of the invention is a kit suitable for PCR, preferably for real-time quantitative PCR (RT-qPCR).

The kit of the present invention can include a support suitable for containing or saving the data and/or information generated with the use of the kit of the invention.

The kit can be used and the use is not particularly limited, although use in any of the embodiments of the method of the invention is preferred. The invention preferably comprises the use of the kit of the invention in predicting the risk of recurrence of breast cancer in subjects who are suffering/have suffered from breast cancer, and/or in classifying a subject into one of two groups, as described in the embodiments of the present invention.

Method of Treating and Preventing the Recurrence of Breast Cancer Using the miRNAs of the Invention A fifth aspect of the present invention provides a method for treating or preventing the recurrence of breast cancer in a subject with breast cancer.

The method of treating breast cancer comprises administering to the subject suffering from breast cancer at least one miRNA preferably selected from the following miRNAs: SEQ ID NO: 1 (miR-149-5p); SEQ ID NO: 2 (miR-10a-5p); SEQ ID NO: 3 (miR-20b-5p); SEQ ID NO: 4 (miR-30a-3p); SEQ ID NO: 5 (miR-342-5p).

The method of treating breast cancer comprises administering to the subject suffering from breast cancer a pharmaceutical composition comprising at least one miRNA preferably selected from the following miRNAs: SEQ ID NO: 1 (miR-149-5p); SEQ ID NO: 2 (miR-10a-5p); SEQ ID NO: 3 (miR-20b-5p); SEQ ID NO: 4 (miR-30a-3p); SEQ ID NO: 5 (miR-342-5p).

When clinical applications are contemplated, the pharmaceutical compositions can be prepared in a suitable form for the intended application. This will generally involve preparing compositions that are essentially pyrogen-free and also free of other impurities that may be harmful to humans. Colloidal dispersion systems, such as macromolecule complexes, nanocapsules, microspheres, beads and lipid-based systems, including oil-in-water emulsions, micelles, mixed micelles and liposomes, can be used as vehicles for administering the microRNAs. The preparation and use of such systems are well known in the art.

Suitable salts and buffers will generally be used so that the transport vectors are stable and access the target cells (tumor cells). The compositions of the present invention comprise an effective amount of the transport vector (including miRNA or naked miRNA), dissolved or dispersed in a pharmaceutically acceptable carrier or in an aqueous medium. The terms "pharmaceutically acceptable" or "pharmacologically acceptable" refer to molecular entities and compositions that do not cause adverse reactions, allergic reactions, etc., when administered to humans. As it is used in the present specification, "pharmaceutically acceptable vehicle" includes solvents, buffers, solutions, dispersion media, coatings, antibacterial and antifungal agents and the like that are acceptable for use in pharmaceutical products, such as pharmaceutical products suitable for administration in humans. The use of such media and agents for pharmaceutically active substances is well known in the art. Except where a conventional medium or agent is incompatible with the active ingredients of the present invention (the miRNAs), the use thereof in the therapeutic compositions is contemplated. Supplementary active ingredients can also be incorporated in the compositions of the present invention provided that they do not deactivate the nucleic acids (miRNAs). The active compositions of the present invention can include conventional pharmaceutical preparations.

The administration of these compositions according to the present invention can be through any common administration route provided that the target tissue is available through that route. This includes oral, nasal, or buccal administration. Alternatively, administration can be by means of intradermal, transdermal, subcutaneous, intramuscular, intraperitoneal or intravenous injection, or by means of direct injection into the breast tumor. Such compositions would usually be administered as pharmaceutically acceptable compositions, as described above. The active compounds can also be administered parenterally or intraperitoneally.

The amount of active ingredient (miRNA(s)) administered to the subject in question can be determined empirically.

The present invention therefore provides at least one miRNA preferably selected from the following miRNAs: SEQ ID NO: 1 (miR-149-5p); SEQ ID NO: 2 (miR-10a-5p); SEQ ID NO: 3 (miR-20b-5p); SEQ ID NO: 4 (miR-30a-3p); SEQ ID NO: 5 (miR-342-5p) for use in a method of treating breast cancer, or alternatively for use in a method of preventing the recurrence of breast cancer.

Therefore, the present invention provides the use of at least one miRNA preferably selected from the following miRNAs: SEQ ID NO: 1 (miR-149-5p); SEQ ID NO: 2 (miR-10a-5p); SEQ ID NO: 3 (miR-20b-5p); SEQ ID NO: 4 (miR-30a-3p); SEQ ID NO: 5 (miR-342-5p) in the elaboration of a medicinal product for treating breast cancer, or alternatively for preventing the recurrence of breast cancer.

EXAMPLES

Example 1: Materials and Methods

Samples from Patients

Seventy-five patients with breast cancer included in the study were subjected to surgery for removing the primary tumor in Hospital Universitario Virgen de la Victoria (HUVV, Malaga, Spain) at some point during the period of 1998-2005. All the patients gave their written informed consent to be included in the study, which was approved by the hospital's Clinical Research Ethics Committee (CREC). The patients were treated uniformly and follow-up was conducted according to the protocols established by the Clinical Oncology Department, based on scientific evidence and international recommendations. All the clinical research was conducted according to the principles expressed in the Declaration of Helsinki. No patient received neoadjuvant therapy. The clinicopathological data and follow-up information were obtained for each patient by means of going over their medical records.

Immunohistochemistry

Formalin-fixed and paraffin-embedded (FFPE) tumors (n=75) were obtained from the hospital's archives. The most representative areas of each tumor were selected by a pathologist and tissue microarrays were constructed for depositing the samples in them in triplicate (circular sections 0.6 mm in diameter). The tumors were previously classified by means of immunohistochemistry, according to the so-called intrinsic subtypes (luminal A, luminal B, basal-like and Her-2+). To that end, antibodies specific for the estrogen receptor (ER, clone SP1), progesterone receptor (PR, clone Y85), Ki-67 (clone SP6), epidermal growth factor receptor 1 (EGFR1, clone EP38Y), vascular endothelial growth factor (VEGF, clone EP1176Y) and cytokeratin 5/6 (CK5/6, clone D5/16B4) were used. The mentioned antibodies were all acquired through the supplier Maestro Diagnostica (Spain). The expression level of HER2 was also determined by means of immunostaining using the HercepTest™ commercial assay (Dako, Denmark). Interpretation of the immunohistochemistry data was carried out according to previously defined criteria [Nielsen T O, Hsu F D, Jensen K, Cheang M, Karaca G, et al. (2004) Immunohistochemical and clinical characterization of the basal-like subtype of invasive breast carcinoma. Clin Cancer Res 10: 5367-5374; Wolff A C, Hammond M E, Schwartz J N, Hagerty K L, Allred D C, et al. (2007) American Society of Clinical Oncology/College of American Pathologists guideline recommendations for human epidermal growth factor receptor 2 testing in breast cancer. J Clin Oncol 25: 118-145; Cheang M C, Voduc D, Bajdik C, Leung S, McKinney S, et al. (2008) Basal-like breast cancer defined by five biomarkers has superior prognostic value than triple-negative phenotype. Clin Cancer Res 14: 1368-1376] by two pathologists who did not know the clinicopathological features and the clinical progression of each patient.

RNA Extraction and Microarray Hybridization

Areas of tumors with more than 90% tumor cells were selected from the paraffin (FFPE) blocks. The cells were manually microdissected from 3 10 micron sections for each tumor. Total RNA was extracted using the commercial nucleic acid isolation system called RecoverAll Total Nucleic Acid Isolation kit (Life Technologies, Grand Island, N.Y., USA). The RNA was converted into in complementary DNA (cDNA) by means of an in vitro reverse transcription reaction, and the cDNA was hybridized on an Affymetrix miRNA chip 2.0 microarray (Affymetrix, Santa Clara, Calif., USA). Both the hybridization and the detection of the hybridization signal were done in the Functional Genomics facility (Instituto de Investigacion Biomédica (IRB), Barcelona, Spain), as an external service and following the recommendations of the manufacturer, Affymetrix.

Microarray Data Analysis

All the statistical analyses were performed using the open-source R programming environment, together with the Bioconductor algorithms package [Gentleman R C, Carey V J, Bates D M, Bolstad B, Dettling M, et al. (2004) Bioconductor: open software development for computational biology and bioinformatics. Genome Biol 5: R80]. Quality of the data read off the microRNA chips was first verified, and then the expression of each miRNA was normalized in relation to control miRNA molecules. Although the chip 2.0 miRNAs (Affymetrix) contain probes that are representative of 131 different organisms, only the data corresponding to human probes was taken into account for this analysis. In order to increase the statistical power of the analysis, those miRNAs the variability of expression of which was below a 66% standard deviation threshold were eliminated. The differential expression of normalized data was evaluated by means of two R packages: limma, which is a moderate statistical test based on an empirical Bayes approach [Smyth G K (2004) Linear models and empirical Bayes methods for assessing differential expression in microarray experiments. Stat Appl Genet Mol Biol 3: Article 3] and RankProd, a simple non-parametric statistical method based on an ordering according to the change in expression values (fold change) of the miRNAs [Breitling R, Armengaud P, Amtmann A, Herzyk P (2004) Rank products: a simple, yet powerful, new method to detect differentially regulated genes in replicated microarray experiments. FEBS Lett 573: 83-92]. The multitest effect was corrected by means of adjusting the p-values by means of the Benjamini and Hochberg method. It was considered in this study that the expression of a miRNA was significantly changed provided that the following two criteria were met: i) adjusted p-value ≤0.05, and ii) fold change ≥2. The best candidate miRNAs are that which appeared in both statistical tests. The following independent comparisons were made: B vs. A (B/A), BC vs. A (BC/A) and B vs. AC (B/AC). Group C alone could not be compared with A or B since the data from the miRNA chips corresponding to group C did not provide statistically significant differences. The MIAME (minimum information about a microarray experiment) data obtained from the microarrays (MIAME format) were deposited in the Array-Express public repository of the European Bioinformatics Institute (EBI, United Kingdom) with accession number E-MTAB-1989.

Validation of Candidate miRNAs by Means of RT-qPCR

Ten nanograms (10 ng) of total RNA of each sample of the tumor were used for obtaining cDNA by means of reverse transcription with specific primers and reagents of the commercial system called TaqMan MicroRNA Reverse Transcription kit (Life Technologies, Grand Island, N.Y., USA). Then the PCR products were amplified by means of using the commercial TaqMan microRNA Assay system, using to that end the commercial TaqMan PCR Universal Master Mix reagent. All the assays were performed in triplicate according to the manufacturer's instructions. The relative expression of the miRNAs was calculated using the $\Delta\Delta C_t$ method. The small RNAs (sRNAs) RNU6b and miR-16 were used as a reference for normalization.

Survival Analysis

The survival analysis program in R was used for calculating survival estimates and carrying out multivariate regression analysis [Lumley T (2007) The survival package. R help guide]. The clinicopathological variables and the variables of the expression of miRNA were analyzed, and the cumulative relapse-free survival (relapse-free survival, RFS), defined as the time elapsing from surgery until recurrence, was considered as a clinical assessment criterion in the survival results. Patients who did not relapse or who were lost during follow-up were censored for the analysis. The actuarial survival rate was calculated using the Kaplan-Meier method and the significance of the statistical differences was evaluated by means of log-rank methods and the Tarone-Ware and Peto-Peto tests. A Cox proportional hazards regression model [Cox D R, Oakes D (1984) Analysis of survival data. London; New York: Chapman and Hall. viii, 201 p. p.] was used for examining relationships between RFS and prognostic factors. All the possible combinations of covariates were tested for identifying the best model according to the AIC (Akaike Information Criterion) value [Sakamoto Y, Ishiguro M, Kitagawa G (1986) Akaike information criterion statistics. Tokyo Dordrecht; Boston Hingham, M A: KTK Scientific Publishers; D. Reidel; Sold and distributed in the U.S.A. and Canada by Kluwer Academic Publishers. xix, 290 p. p], which is a measurement of the relative quality of a statistical model. The proportionality of hazard assumption of the Cox models was verified by means of the generalized linear regression test of the scaled Schoenfeld residuals on functions of time [Sakamoto Y, Ishiguro M, Kitagawa G (1986) Akaike information criterion statistics. Tokyo Dordrecht; Boston Hingham, M A: KTK Scientific Publishers; D. Reidel; Sold and distributed in the U.S.A. and Canada by Kluwer Academic Publishers. xix, 290 p. p]. A non-zero slope indicates a violation of the proportional hazard hypothesis, and therefore its exclusion from the analysis.

Prediction Model of the 5-miRNA Signature

Three steps are involved in estimating the expression profiles for generating a predictor suitable for future observations: selection of the model, evaluation of the prediction and selection of the function [Molinaro A M, Simon R, Pfeiffer R M (2005) Prediction error estimation: a comparison of resampling methods. Bioinformatics 21: 3301-3307]. The Naïve Bayes classifier was used in this work for predicting the class of future observations. It is a standard model based on the Bayes theorem without domain specific assumptions. With this model, each new sample is classified in the most likely class, according to its probability a posteriori, and is calculated according to the Bayes theorem. This classifier is used for estimating predictive models in intergroup comparisons. The C-index is the most widely accepted measurement for the discrimination capacity of a predictive model. In binary cases, this metric is equivalent to the area under the curve (AUC) in a receiver operating characteristic curve, which is commonly used for measuring the predictive capacity of logistic regression models. For evaluating precision of the prediction of the Naïve Bayes classifiers in TPR, FPR and ROC curves, a generalized bootstrap estimate of the classification error 0.632+ was used [Efron B, Tibshirani R (1993) An introduction to the bootstrap. New York: Chapman & Hall. xvi, 436 p. p]. The bootstrap estimator is obtained by means of drawing routine samples B having size N with replacement. The observations in the starting samples are used for training, whereas the remaining observations (the out-of-bag sample) are used for the test. Performance estimates were averaged for each prediction on all the out-of-bag samples, and the starting estimate of the TPR, FPR and ROC curves is defined similarly to the starting error. e1071 packets [Gentleman R C, Carey V J, Bates D M, Bolstad B, Dettling M, et al. (2004) Bioconductor: open software development for computational biology and bioinformatics. Genome Biol 5: R80] and Daim packets (http://CRAN.R-project.org/package=Daim) were used in R to conduct these analyses. The selection of features refers to deciding which miRNAs will be included in the prediction, and it is a crucial step in developing a predictive class. Too many features could even reduce precision of the model and can lead to excessively adjusted data [Ransohoff D F (2004) Rules of evidence for cancer molecular-marker discovery and validation. Nat Rev Cancer 4: 309-314]. To avoid this, all miRNA combinations were tested for identifying the model containing the expression pattern of miRNA which more precisely predicts the groups in a situation of risk.

Prediction of miRNA Target Genes

The mirTarBase database (http://mirtarbase.mbc.nct-u.edu.tw/) [Hsu S D, Lin F M, Wu W Y, Liang C, Huang W C, et al. (2011) miRTarBase: a database curates experimentally validated microRNA-target interactions. Nucleic Acids Res 39: D163-169] and miRecords database (http://mirecords.biolead.org/) [Xiao F, Zuo Z, Cai G, Kang S, Gao X, et al. (2009) miRecords: an integrated resource for microRNA-target interactions. Nucleic Acids Res 37: D105-110], were used for identifying the messenger RNA (mRNA) molecules experimentally validated as a target of each of the miRNAs of the 5-miRNA signature. Both databases contain experimentally validated data about functional miRNA/target mRNA interactions. In order to graphically display the miRNA/mRNA relationships, the CyTargetLinker plug-in was used in the Cytoscape display program [Shannon P, Markiel A, Ozier O, Baliga N S, Wang J T, et al. (2003) Cytoscape: a software environment for integrated models of biomolecular interaction networks. Genome Res 13: 2498-2504]. The ClueGo plug-in and CluePedia plug-ins [Bindea G, Mlecnik B, Hackl H, Charoentong P, Tosolini M, et al. (2009) ClueGO: a Cytoscape plug-in to decipher functionally grouped gene ontology and pathway annotation networks. Bioinformatics 25: 1091-1093; Bindea G, Galon J, Mlecnik B (2013) CluePedia Cytoscape plug-in: pathway insights using integrated experimental and in silico data. Bioinformatics 29: 661-663] were used to retrieve the Gene Ontology (GO) associated with the target mRNAs identified with CyTargetLinker [Kutmon M, Kelder T, Mandaviya P, Evelo C T, Coort S L (2013) CyTargetLinker: A Cytoscape App to Integrate Regulatory Interactions in Network Analysis. PLoS One 8: e82160]. Only those GO terms with p-value <0.01, corrected by the Benferroni method, were considered.

Example 2: Microarray Analysis

For identifying the miRNAs associated with early and late recurrence, the abundance of 1105 miRNAs was analyzed in a cohort of 75 primary breast tumors by microarray technology. The tumors were classified into three prognosis groups according to the clinical progression of the patients as follows: Group A, patients who were disease-free 60 months after removal of the tumor; Group B, patients who developed early recurrence (24 months after surgery); and Group C, patients who developed late recurrence (50-60 months after surgery). Table 3 summarizes the clinicopathological data of the study population. Except for group C, the cohort was balanced for the 4 intrinsic subtypes: luminal A type, luminal B type, basal-like type and HER2+. The last two subtypes are associated with a more aggressive phenotype and a higher risk of relapse [24, 26], which explains why group C (late recurrence) is primarily made up of luminal tumors (Table 3).

TABLE 3

Clinicopathological features of the study population

| | | Group A* | | Group B* | | Group C* | | p-value |
|---|---|---|---|---|---|---|---|---|
| | | n | (%) | n | (%) | n | (%) | |
| Number of patients | | 36 | (48.0) | 27 | (36.0) | 12 | (16.0) | |
| Age | ≤50 | 15 | (45.5) | 10 | (37.0) | 4 | (36.4) | 0.8034 |
| | >50 | 18 | (54.5) | 17 | (63.0) | 7 | (63.6) | |
| Hormone status | Pre/perim.** | 15 | (41.7) | 10 | (37.0) | 6 | (50.0) | |
| | Postmen.** | 21 | (58.3) | 15 | (55.6) | 6 | (50.0) | |
| | Unknown | 0 | (0.0) | 2 | (7.4) | 0 | (0.0) | |
| Tumor size (cm) | <2 | 5 | (15.2) | 2 | (7.4) | 3 | (27.3) | 0.7487 |
| | 2-5 | 22 | (66.7) | 17 | (63.0) | 7 | (63.6) | |
| | >5 | 5 | (15.2) | 4 | (14.8) | 1 | (9.1) | |
| | Unknown | 1 | (3.0) | 4 | (14.8) | 0 | (0.0) | |
| Tumor stage | I | 3 | (8.3) | 4 | (14.8) | 1 | (8.3) | |
| | II | 19 | (52.8) | 8 | (29.6) | 8 | (66.7) | |
| | III | 14 | (38.9) | 15 | (55.6) | 3 | (25.0) | |
| Histological grade | 1 | 4 | (11.1) | 0 | (0.0) | 0 | (0.0) | |
| | 2 | 14 | (38.9) | 16 | (59.3) | 9 | (75.0) | |
| | 3 | 16 | (44.4) | 8 | (29.6) | 2 | (16.7) | |
| | Unknown | 2 | (5.6) | 3 | (11.1) | 1 | (8.3) | |
| Histological subtype | Lobular | 4 | (11.1) | 0 | (0.0) | 0 | (0.0) | |
| | Ductal | 29 | (80.6) | 24 | (88.9) | 11 | (91.7) | |
| | Medullary | 0 | (0.0) | 1 | (3.7) | 0 | (0.0) | |
| | Carcinoma | 1 | (2.8) | 2 | (7.4) | 0 | (0.0) | |
| | Mixed | 2 | (5.6) | 0 | (0.0) | 1 | (8.3) | |
| Intrinsic subtype | Luminal A | 9 | (25.0) | 3 | (11.1) | 7 | (58.3) | |
| | Luminal B | 9 | (25.0) | 6 | (22.2) | 3 | (25.0) | |
| | Basal-like | 9 | (25.0) | 9 | (33.3) | 1 | (8.3) | |
| | HER2-enriched | 9 | (25.0) | 9 | (33.3) | 1 | (8.3) | |
| Type of surgery | Conserving | 22 | (61.1) | 9 | (33.3) | 5 | (41.7) | |
| | Radical | 14 | (38.9) | 18 | (66.7) | 7 | (58.3) | |
| Lymph node affected | Negative | 14 | (42.4) | 18 | (48.6) | 5 | (45.5) | 0.0292 |
| | 1-3 | 13 | (39.4) | 5 | (13.5) | 5 | (45.5) | |
| | ≥4 | 6 | (12.8) | 14 | (37.8) | 1 | (9.1) | |
| Therapy | Chem.*** | 28 | (77.8) | 23 | (85.2) | 7 | (58.3) | |
| | Horm.*** | 20 | (55.6) | 15 | (55.6) | 10 | (83.3) | |
| | Rad.*** | 25 | (69.4) | 13 | (48.1) | 6 | (50.0) | |

The microarrays were analyzed for the first time for quality control and were normalized for expression of the miRNA genes (see Example 1). Four samples with a poor signal quality were excluded from the study, leaving a cohort of 71 breast tumors for later analysis.

The unsupervised hierarchical clustering of the microarray data showed that the transcription profiles of the miRNAs discriminate the prognosis groups into two different clusters (groups) (FIG. 2). Cluster 1 includes 70% of all tumors of group A and 26% of all tumors of group B, whereas cluster 2 includes 74% of all tumors of group B and 30% of all tumors of group A. Tumors of group C were generally distributed within clusters 1 and 2, with a slightly higher proportion (63%) of tumors grouped in cluster 2. Since group C represents an intermediate clinical state between non-recurrence (group A) and early recurrence (group B), the broad distribution of tumors of group C within groups 1 and 2 could reflect the same variation at molecular level. An alternative explanation could be that group C cannot be identified by a single miRNA signature, either due to its intrinsic molecular nature or to a smaller sample size. It should be pointed out that the tumors tend to be grouped according to their ER status ("ER+" or "ER−"), and therefore most luminal tumors ("ER+") were grouped in cluster 1, whereas cluster 2 primarily brought together HER2+ tumors and basal-like tumors, which are both "ER−" (FIG. 2). Multiple pairwise comparison test showed that the greater differences in expression occurred between luminal A type tumors and basal-like tumors. Accordingly, the longest list of possible candidate miRNAs was obtained by comparing luminal A type tumors and basal-like tumors or basal-like tumors and other subtypes (Table 4). These results suggest that the three tumor groups (A, B and C) represent different biological entities.

TABLE 4

Most significantly deregulated miRNAs in breast tumors of the different intrinsic subtypes

| ID | Luminal A vs Basal-like | | Luminal A vs HER2 | | Lumial B vs Basal-like | | Luminal B vs HER2 | | Luminal A vs others | | Basal-like vs others | |
|---|---|---|---|---|---|---|---|---|---|---|---|---|
| | logFC | adj. P. Val | logFC | adj. P. Val | logFC | adj. P. Val | logFC | adj. P. Val | logFC | adj. P. Val | logFC | adj. P. Val |
| hsa-miR-342-3p | 2.01 | 1.29E−07 | 1.89 | 8.31E−07 | 1.72 | 1.76E−05 | 1.60 | 0.00 | 1.42 | 1.02E−05 | −1.27 | 1.45E−04 |
| hsa-miR-342-5p | 2.22 | 2.52E−04 | 2.01 | 2.21E−03 | 1.95 | 2.38E−03 | 1.74 | 0.01 | 1.52 | 8.54E−03 | −1.45 | 4.47E−03 |
| hsa-miR-29b-2-5p | 1.45 | 7.39E−03 | 1.27 | 3.98E−02 | 1.92 | 4.73E−04 | | | | | | |
| hsa-miR-18a | −2.15 | 4.54E−04 | | | −1.61 | 2.81E−02 | | | | | 1.62 | 1.96E−03 |
| hsa-miR-934 | −1.51 | 1.00E−03 | | | −1.37 | 6.97E−03 | | | | | 1.37 | 4.19E−04 |
| hsa-miR-193b | 1.27 | 7.80E−03 | | | 1.36 | 7.97E−03 | | | | | | |
| hsa-miR-375 | 3.10 | 4.38E−03 | | | 3.60 | 1.33E−03 | | | | | −3.01 | 6.65E−04 |
| hsa-miR-146a | −1.60 | 2.26E−02 | | | | | | | | | 1.34 | 1.92E−02 |
| hsa-miR-362-5p | −1.38 | 4.61E−03 | | | | | | | | | 0.90 | 4.01E−02 |
| hsa-miR-20a | −1.27 | 1.55E−03 | | | | | | | | | 1.01 | 2.89E−03 |
| hsa-miR-17 | −1.32 | 2.52E−04 | | | | | | | | | | |
| hsa-miR-106a | −1.30 | 4.32E−04 | | | | | | | | | | |
| hsa-miR-505-5p | −1.29 | 4.38E−03 | | | | | | | | | | |
| hsa-miR-17-3p | −1.08 | 3.33E−02 | | | | | | | | | | |
| hsa-miR-30a | | | 1.86 | 4.91E−03 | | | 1.51 | 0.02 | | | | |
| hsa-miR-612 | | | −1.16 | 4.33E−02 | | | | | | | | |
| hsa-miR-1308 | | | −1.03 | 4.91E−03 | | | | | | | | |
| hsa-miR-30c | | | 1.14 | 4.12E−02 | | | | | | | | |
| hsa-miR-141 | | | 1.41 | 4.09E−02 | | | | | | | | |
| hsa-miR-30a-3p | | | 1.98 | 3.11E−02 | | | | | | | | |
| hsa-miR-224-3p | | | | | | | −1.29 | 0.03 | | | | |
| hsa-miR-125a-5p | | | | | | | 1.03 | 0.02 | | | | |
| hsa-miR-193b | | | | | | | 1.09 | 0.03 | | | | |
| hsa-miR-29b-2-5p | | | | | | | 1.74 | 0.00 | | | −1.17 | 9.67E−03 |
| hsa-miR-149 | | | | | | | | | | | −1.33 | 3.46E−02 |
| hsa-miR-425 | | | | | | | | | | | −0.77 | 4.01E−02 |
| hsa-miR-99b | | | | | | | | | | | −0.60 | 2.19E−02 |
| hsa-miR-1975 | | | | | | | | | | | −0.41 | 4.01E−02 |
| hsa-miR-18a-3p | | | | | | | | | | | 0.54 | 4.01E−02 |
| hsa-miR-18b | | | | | | | | | | | 0.73 | 1.92E−02 |
| hsa-miR-19b | | | | | | | | | | | 0.94 | 4.16E−02 |

For selecting the miRNAs of FIG. 2 having a statistically significant and differential expression, multiple and pairwise comparisons were made between prognosis groups A, B and C. To that end, two different approaches were used, i.e., limma and RankProd Bioconductor. Only those candidates with a change (EC, fold change) >2 (either positively (up) regulated or negatively (down) regulated) and an adjusted p-value (adj-pval)<0.05 were selected (Table 5).

Therefore, the comparison of the p-values obtained with both limma and RankProd log FC libraries led to the identification of miR-149, miR-20b, miR-30a-3p, miR-342-5p, miR-625 and miR-10a as the miRNAs the expression of which changes most significantly when tumors of recurrence-free patients are compared with tumors of patients with recurrence, i.e., group B vs. A or BC vs. A (Table 5). As had been seen in the hierarchical cluster (FIG. 2), the largest

TABLE 5

The most significant negatively regulated miRNAs in tumors in patients with recurrence

| Comparison [#] | miRNA | limma F[*] | | RankProd[] | | RT-qPCR[*] | |
|---|---|---|---|---|---|---|---|
| | | logFC | adj-pval | logFC | adj-pval | logFC | SE |
| B/A | hsa-miR-149 | −1.410 | 0.0016 | −1.615 | <0.00001 | −2.646 | 0.724 |
| | hsa-miR-20b | −1.048 | 0.0071 | −1.237 | <0.00001 | −1.542 | 0.521 |
| | hsa-miR-30a-3p | −1.359 | 0.0078 | −1.521 | <0.00001 | −1.001 | 0.514 |
| | hsa-miR-625 | −1.149 | 0.0014 | −1.377 | <0.00001 | −0.347 | 0.282 |
| | hsa-miR-10a | −1.235 | 0.0168 | −1.547 | <0.00001 | −1.108 | 0.404 |
| BC/A | hsa-miR-149 | −1.120 | 0.0117 | −1.329 | <0.00001 | −2.555 | 0.681 |
| | hsa-miR-20b | −1.016 | 0.0076 | −1.155 | <0.00001 | −1.470 | 0.536 |
| | hsa-miR-30a-3p | −1.124 | 0.0256 | −1.326 | <0.00001 | −0.994 | 0.458 |
| | hsa-miR-625 | −1.003 | 0.0049 | −1.223 | <0.00001 | −0.266 | 0.237 |
| B/AC | hsa-miR-149 | −1.294 | 0.0052 | −1.446 | <0.00001 | −2.340 | 0.698 |
| | hsa-miR-10a | −1.397 | 0.0093 | −1.647 | <0.00001 | −1.241 | 0.404 |
| | hsa-miR-342-5p | −1.123 | 0.0159 | −1.254 | <0.00001 | −1.194 | 0.627 |

[#] Group A = non-recurrence, Group B = early recurrence (≤24 months after surgery), Group C = late recurrence (50-60 months after surgery)
[*]limma F, filtered data analysis (sd > 70%) using limma
[**]RankProd, unfiltered data analysis using the RankProduct algorithm
[***]RT-qPCR, the relative expression of the miRNAs was calculated using the $\Delta\Delta C_t$ method. The standard error (SE) was calculated based on the theory of error propagation (Quackenbush (2002) Microarray data normalization and transformation. Nat Genet 32 Suppl: 496-501).

differences in the expression of the six miRNAs were again detected when comparing group B vs. group A (Table 5). In contrast, the pairwise comparisons of any of groups A or B with group C did not result in any statistically significant miRNA. In particular, the relative levels of all candidate miRNAs were lower in the samples of group B compared with others, which suggests that these miRNAs could act either directly or indirectly as metastasis suppressors.

As regards the intrinsic subtypes, low levels of miR-149, miR-30a-3p and miR-342-5p were found in "ER−" tumors (Table 6).

The differential expression of the six miRNAs was also determined by RT-qPCR in the three prognosis groups (Table 5). With the exception of miR-625, which could not be validated, it was confirmed that miR-149-5p, miR-20b-5p, miR10a-5p, miR-30a-3p and miR-342-5p (the "5-miRNA signature" or "signature of the five miRNAs" hereinafter) were negatively regulated in the tumors of patients with recurrence (groups B or C) compared with the expression in tumors of recurrence-free patients (group A, Table 5). miR-625 was excluded from any additional study since the RT-qPCR data showed minimum variation between groups (FC<2). Then the 71 tumors were re-grouped according to the 5-miRNA signature. As shown in FIG. 3, the tumors of groups A and B were clearly separated into two different groups which included most of the samples expected in each category: 78.8% of type A tumors in cluster 1b (risk low) and 70.4% of group B tumors in cluster 2b (high risk). It should be pointed out that supervised analysis includes most tumors of group C (72.8%), in cluster 1b, which indicates that the 5-miRNA signature specifically discriminates tumors with an overall higher risk of early recurrence./*/*

Example 3: Prognostic Value of the Signature of the Five miRNAs

The relationship between expression of the 5-miRNA signature and recurrence-free survival (RFS) was examined by means of survival analysis. FIG. 4A shows a Kaplan-Meier graph for the entire series of patients included in the study. Due to the intrinsic characteristics of the cohort, the drop in RFS is only observed in the intervals of 0-24 and 50-60 months (corresponding to groups B and C, respectively). The tumors were then grouped into two different groups according to their 5-miRNA signature. A first group includes tumors with the five miRNAs negatively regulated simultaneously (FC>2 and p<0.05), and a second group includes those tumors that did not have the five miRNAs negatively regulated simultaneously. Survival analysis was conducted using the clinical data of the corresponding patients. As shown in FIG. 4B, the Kaplan-Meier graphs for both groups show that the 5-miRNA signature defines a "high risk" group of patients with short RFS (Peto-Peto test with p-value=0.02, when comparing low to high risk groups).

All the possible combinations of different covariates (tumor subtype, age of the patient, tumor size, number of lymph nodes affected and the 5-miRNA signature) with early recurrence (≤24 months) were also tested using a Cox proportional hazard regression model for identifying the best prognostic factors. The best model according to the AIC criterion includes tumor size and expression of the 5-miRNA signature (data not shown). Only the 5-miRNA signature (the five negatively regulated miRNAs) was statistically significant in the Cox model for the high risk group (p-value=0.02 with HR=2.73, 95% CI: 1.17-6.36). The data relating to expression of the 5-miRNA was also used to develop a prediction model through bootstrapping in a Naive Bayes classifier (B=200 with N=71, see Example 1, methods). The prognostic precision of the models was evaluated by the ROC (Receiver Operating Characteristic) test (FIG. 5). When considered individually, miR-30a-3p and miR-10a-5p showed a surprisingly high area under the curve (AUC) (0.890 and 0.875, respectively). This result suggests that the target mRNAs regulated by miR-30a-3p and miR-10a-5p could have a higher contribution potential for the final result of the disease. However, the signature of the five miRNAs had the strongest predictive value in relation to discriminating tumors of patients who will develop an early recurrence (group B) from those who will not develop a recurrence (disease-free) (group A), with an AUC=0.993 (FIG. 5). In summary, the signature of the five miRNAs exhibits a high value as a predictor of the risk of early recurrence of breast cancer.

Example 4: Possible Target mRNAs of the 5-miRNA Signature

Existing public databases (MTI) were used. In particular, the validated targets were obtained from miTarBase and miRecords (see Example 1, methods). First a biological network was created in Cytoscape (Shannon P, Markiel A, Ozier O, Baliga N S, Wang J T, et al. (2003) Cytoscape: a software environment for integrated models of biomolecular interaction networks. Genome Res 13: 2498-2504), which contains all the individual miRNAs included in the 5-miRNA signature: miR-149-5p, miR-10a-5p, miR-20b-5p, miR-30a-3p and miR-342-5p). Then the network was enlarged by means of adding *H. sapiens* MTI data retrieved from the indicated depositories, and finally extended regulatory interaction networks (RIN) were generated and displayed in Cytoscape. Each regulatory interaction in the network consists of two nodes, a regulatory component (miRNA) and a target biomolecule (mRNA) connected through a directed edge. FIG. 6 shows the extended network when the RIN threshold is set to 1 (i.e., each predicted target appears in at least one RIN). Therefore, with RIN=1 the network included 14 validated targets assigned to miR-20b-5p ((VEGFA, BAMBI, EFNB2, MYLIP, CRIM1, ARID4B, HIF1A, HIPK3, CDKN1A, PPARG, STAT3, MUC17, EPHB4, and ESR1), seven validated targets assigned to miR-10a-5p (HOXA1, NCOR2, SRSF1, SRSF10/TRA2B, MAP3K7, USF2 and BTRC) and nine validated targets assigned to miR-30a-3p (THBS1, VEZT, TUBA1A, CDK6, WDR82, TMEM2, KRT7, CYR61 and SLC7A6) (FIG. 5). Taking these results into account and taking into account that i) the extended network was constructed considering the 5-miRNA signature as the network nodes, and ii) all the MTIS depicted in FIG. 6 have been experimentally verified, it is suggested that at least some of the 30 mRNAs (FIG. 6) can be regulated in viva by means of the 5-miRNA signature in tumors with early recurrence.

In order to better understand the molecular bases of the prognostic value of the 5-miRNA signature, the biological processes associated with the 30 experimentally verified targets of FIG. 6 were investigated. To that end, Gene Ontology (GO) term searches and key protein searches in the KEGG (Kyoto Encyclopedia of Genes and Genomes) server associated with the 30 target mRNAs as a whole were conducted. However, it should be pointed out that a restrictive approach was applied, including only targets of the experimentally validated miRNAs—miR-149 and miR-342-5p were not included in the GO analysis- and therefore additional biological pathways could be affected by the negative regulation of the 5-miRNA signature. To increase the predictive value of the GO analysis, only ontology terms with experimental evidence and a p-value ≤0.01 were considered. Oddly enough, most targets in the set were associated with GO terms related to angiogenesis and cell migration (GO: 0001954, GO: 0002040, GO: 0002042, GO: 0043534 and GO: 0043536), in addition to the GO terms "response to estradiol stimulus" (GO: 0032355), "monocyte differentiation" (GO: 0030224) and "ephrin" receptor signaling pathway" (GO: 0048013) (FIG. 7). Other GO terms that were particularly relevant for the study were: "positive regulation of fibroblast proliferation" (GO: 0048146) "regulation of chemotaxis" (GO: 0050920), "regulation of cellular response to growth factor stimulus" (GO: 0090287) and "positive regulation of reactive oxygen species metabolic process" (GO: 2000379). Overall, the computational analysis of the assumed mRNA targets experimentally verified for the 5-miRNA signature and their associated GO terms (p-value ≤0.01) suggest that early recurrence in breast cancer is a consequence of the higher angiogenic, invasive and proliferative potential of a subgroup of tumors with lower levels of at least miR-20b-5p, miR-10a-5p and miR-30a-3p (FIG. 6). In fact, the integration of GO terms in KEGG pathway maps supports this hypothesis since the net effect of changes in regulation pathways affected by an increase in the expected targets would be an increase in both proliferation and angiogenesis (FIG. 9).

In an effort to validate this hypothesis, retrospective immunohistochemistry data for the expression of angiogenesis markers (VEGF) and proliferation markers (Ki67) in the set of primary tumors (Table 5) was collected, provided this was possible. Expression data in relation to estrogen receptors (ER) was included as a positive control since they are often associated with the prognosis [3, 4]. Given that the low expression of miRNA genes must give rise to an increase in the stability of their target mRNAs, an increase in the expression of VEGF and Ki67 in those tumors identified by the signature (high risk group) of the five miRNAs is envisaged. The quantification of VEGF, Ki67 and ER immunostaining was conducted as previously described [Nielsen T O, Hsu F D, Jensen K, Cheang M, Karaca G, et al. (2004) Immunohistochemical and clinical characterization of the basal-like subtype of invasive breast carcinoma. Olin Cancer Res 10: 5367-5374; Wolff A C, Hammond M E, Schwartz J N, Hagerty K L, Allred D C, et al. (2007) American Society of Clinical Oncology/College of American Pathologists guideline recommendations for human epidermal growth factor receptor 2 testing in breast cancer. J Olin Oncol 25: 118-145; Cheang M C, Voduc D, Bajdik C, Leung S, McKinney S, et al. (2008) Basal-like breast cancer defined by five biomarkers has superior prognostic value than triple-negative phenotype. Olin Cancer Res 14: 1368-1376) and the percentage of tumors showing low or high expression of each marker for each prognosis group (A, B or C) or the status of the 5-miRNA signature (low or high risk) was calculated. The results of the analysis are summarized in Table 6.

TABLE 6

Expression levels of VEGF, Ki67 and ER in tumors

| | | Group | | | | Risk level | | |
|---|---|---|---|---|---|---|---|---|
| | | A n (%) | B n (%) | C n (%) | p-val | Low n (%) | High n (%) | p-val |
| VEGF | Low | 6 (20.7) | 4 (15.4) | 1 (9.1) | NS | 14 (37.8) | 5 (17.2) | NS |
| | High | 23 (79.3) | 22 (84.6) | 10 (90.9) | | 23 (62.2) | 24 (82.8) | |
| Ki67 | Neg. | 15 (45.4) | 4 (14.8) | 6 (54.5) | 0.012 | 17 (40.5) | 8 (25.6) | NS |
| | Pos. | 18 (54.6) | 23 (85.2) | 5 (45.5) | | 25 (59.5) | 21 (72.4) | |
| ER | Neg. | 17 (51.5) | 18 (66.7) | 2 (18.2) | 0.025 | 14 (33.3) | 23 (79.3) | <0.0001 |
| | Pos. | 16 (48.5) | 9 (33.3) | 9 (81.8) | | 28 (66.7) | 6 (20.7) | |

Only a statistically significant association was observed when comparing Ki67 vs. prognosis groups (p-value=0.012), ER vs. prognosis groups (p-value=0.025) or ER vs. risk groups (p-value <0.0001). In contrast, a significant relationship between the expression of VEGF with any of the prognosis groups or the 5-miRNA signature was not observed (Table 6). Nevertheless, a slight increase in VEGF and Ki67 levels was observed in tumors with early recurrence (group B) and in the "high risk" group (Table 6). A survival analysis also showed a drop in RFS in those patients with tumors positive for Ki67, negative for ER and with an increase in the expression of VEGF (FIG. 8). Once again, however, only Ki67 levels were significantly associated with RFS (F=0.044, FIG. 8, central panel).

It has been demonstrated herein that the primary tumors of patients with early recurrences are different from the tumors of recurrence-free patients, at least in relation to their miRNA profile. These differences in the expression of miRNA—which must also have an impact on the tumor transcriptome—reflect two different biological entities with at least a different proliferative potential (FIG. 8). The present analysis of networks predicted several targets which could also confer a higher angiogenic and invasive capacity to tumors with an early recurrence. These results demonstrate that breast tumors with a different risk of recurrence can be distinguished by the expression level of miRNA (of the signature of the five miRNAs, including miR-149, miR-30a-3p, miR-20b, miR-10a and miR-342-5p). These miRNAs exhibit a high prognostic value (AUC=0.993, p-value <0.05) and are negatively regulated in primary breast tumors of patients who develop an early recurrence. Furthermore, a set of 30 mRNAs regulated by the 5-miRNA signature has been identified in tumors showing early recurrence. It should be pointed out that the set includes the mRNAs coding for proteins primarily involved in angiogenesis and proliferation (VEGFA, THBS1, EPHB4 CDK6 and DCKN1, among others). It has been demonstrated that recurrent primary tumors have a higher significant proliferative potential, measured by Ki67 immunostaining.

REFERENCES

1. Fisher E R, Palekar A S, Gregorio R M, Redmond C, Fisher B (1978) Pathological findings from the national 1. surgical adjuvant breast project (Protocol No. 4). IV. Significance of tumor necrosis. Hum Pathol 9: 523-530.
2. Elston C W, Ellis I O (1991) Pathological prognostic factors in breast cancer. I. The value of histological grade in breast cancer: experience from a large study with long-term follow-up. Histopathology 19: 403-410.
3. Perou C M, Sorlie T, Eisen M B, van de Rijn M, Jeffrey S S, et al. (2000) Molecular portraits of human breast tumours. Nature 406: 747-752.
4. Sorlie T, Perou C M, Tibshirani R, Aas T, Geisler S, et al. (2001) Gene expression 12 patterns of breast carcinomas distinguish tumor subclasses with clinical implications. Proc Natl Acad Sci USA 98: 10869-10874.
5. Spitale A, Mazzola P, Soldini D, Mazzucchelli L, Bordoni A (2009) Breast cancer classification according to immunohistochemical markers: clinicopathologic features and short-term survival analysis in a population-based study from the South of Switzerland. Ann Oncol 20: 628-635.
6. Steeg P S (2006) Tumor metastasis: mechanistic insights and clinical challenges. Nat Med 12: 895-904.
7. Chiang A C, Massague J (2008) Molecular basis of metastasis. N Engl J Med 359: 2814-2823.
8. Saphner T, Tormey D C, Gray R (1996) Annual hazard rates of recurrence for breast cancer after primary therapy. J Clin Oncol 14: 2738-2746.
9. Demicheli R, Abbattista A, Miceli R, Valagussa P, Bonadonna G (1996) Time distribution of the recurrence risk for breast cancer patients undergoing mastectomy: further support about the concept of tumor dormancy. Breast Cancer Res Treat 41: 177-185.
10. Jatoi I, Tsimelzon A, Weiss H, Clark G M, Hilsenbeck S G (2005) Hazard rates of recurrence following diagnosis of primary breast cancer. Breast Cancer Res Treat 89: 173-178.
11. Demicheli R, Retsky M W, Hrushesky W J, Baum M (2007) Tumor dormancy and surgery-driven interruption of dormancy in breast cancer: learning from failures. Nat Clin Pract Oncol 4: 699-710.
12. Demicheli R, Hrushesky W J, Retsky M W, Bonadonna G, Valagussa P (2007) Comment to "Effect of primary tumor extirpation in breast cancer patients who present with stage IV disease and intact primary tumor" by G V Babiera, R Rao, L Feng, F Meric-Bernstam, H M Kuerer, S E Singletary, K K Hunt, M I Ross, K M Gwyn, B W Feig, F C Ames, G N Horthobagyi. Ann Surg Oncol 2006; 13:776-782. Ann Surg Oncol 14: 1519-1520.
13. Demicheli R, Retsky M W, Hrushesky W J, Baum M, Gukas I D (2008) The effects of surgery on tumor growth: a century of investigations. Ann Oncol 19: 1821-1828.
14. Demicheli R, Valagussa P, Bonadonna G (2001) Does surgery modify growth kinetics of breast cancer micrometastases? Br J Cancer 85: 490-492.
15. Hess K R, Pusztai L, Buzdar A U, Hortobagyi G N (2003) Estrogen receptors and distinct patterns of breast cancer relapse. Breast Cancer Res Treat 78: 105-118.
16. Demicheli R, Biganzoli E, Ardoino I, Boracchi P, Coradini D, et al. (2010) Recurrence and mortality dynamics for breast cancer patients undergoing mastectomy according to estrogen receptor status: different mortality but similar recurrence. Cancer Sci 101: 826-830.
17. Perez-Rivas L G, Jerez J M, Fernandez-De Sousa C E, de Luque V, Quero C, et al. (2012) Serum protein levels following surgery in breast cancer patients: a protein microarray approach. Int J Oncol 41: 2200-2206.
18. Carlsson A, Wingren C, Kristensson M, Rose C, Ferno M, et al. (2011) Molecular serum portraits in patients with primary breast cancer predict the development of distant metastases. Proc Natl Acad Sci USA 108: 14252-14257.
19. Pietrowska M, Polanska J, Marczak L, Behrendt K, Nowicka E, et al. (2010) Mass spectrometry-based analysis of therapy-related changes in serum proteome patterns of patients with early-stage breast cancer. J Transl Med 8: 66.
20. Rouzier R, Perou C M, Symmans W F, Ibrahim N, Cristofanilli M, et al. (2005) Breast cancer molecular subtypes respond differently to preoperative chemotherapy. Clin Cancer Res 11: 5678-5685.
21. Nielsen T O, Parker J S, Leung S, Voduc D, Ebbert M, et al. (2010) A comparison of PAM50 intrinsic subtyping with immunohistochemistry and clinical prognostic factors in tamoxifen-treated estrogen receptor-positive breast cancer. Clin Cancer Res 16: 5222-5232.
22. Cheang M C, Chia S K, Voduc D, Gao D, Leung S, et al (2009) Ki67 index, HER2 status, and prognosis of patients with luminal B breast cancer. J Natl Cancer Inst 101: 736-750.
23. Cheang M C, Voduc D, Bajdik C, Leung S, McKinney S, et al. (2008) Basal-like breast cancer defined by five biomarkers has superior prognostic value than triple-negative phenotype. Clin Cancer Res 14: 1368-1376.
24. Kennecke H, Yerushalmi R, Woods R, Cheang M C, Voduc D, et al. (2010) Metastatic behavior of breast cancer subtypes. J Clin Oncol 28: 3271-3277.
25. Parker J S, Mullins M, Cheang M C, Leung S, Voduc D, et al. (2009) Supervised risk predictor of breast cancer based on intrinsic subtypes. J Clin Oncol 27:1160-1167.
26. Voduc K D, Cheang M C, Tyldesley S, Gelmon K, Nielsen T O, et al. (2010) Breast cancer subtypes and the risk of local and regional relapse. J Clin Oncol 28: 1684-1691.
27. Curtis C, Shah S P, Chin S F, Turashvili G, Rueda O M, et al. (2012) The genomic and transcriptomic architecture of 2,000 breast tumours reveals novel subgroups. Nature 486: 346-352.
28. Dawson S J, Rueda O M, Aparicio S, Caldas C (2013) A new genome-driven integrated classification of breast cancer and its implications. EMBO J 32: 617-628.
29. Bartel D P (2009) MicroRNAs: target recognition and regulatory functions. Cell 136: 215-233.
30. Djuranovic S, Nahvi A, Green R (2011) A parsimonious model for gene regulation by miRNAs. Science 331: 550-553.
31. Lund E, Guttinger S, Calado A, Dahlberg J E, Kutay U (2004) Nuclear export of microRNA precursors. Science 303: 95-98.
32. Brodersen P, Voinnet O (2009) Revisiting the principles of microRNA target recognition and mode of action. Nat Rev Mol Cell Biol 10: 141-148.
33. Carthew R W, Sontheimer E J (2009) Origins and Mechanisms of miRNAs and siRNAs. Cell 136: 642-655.
34. Huntzinger E, Izaurralde E (2011) Gene silencing by microRNAs: contributions of translational repression and mRNA decay. Nat Rev Genet 12: 99-110.
35. Griffiths-Jones S, Saini H K, van Dongen S, Enright A J (2008) miRBase: tools for microRNA genomics. Nucleic Acids Res 36: D154-158.
36. Croce C M (2009) Causes and consequences of microRNA dysregulation in cancer. Nat Rev Genet 10: 704-714.
37. Volinia S, Calin G A, Liu C G, Ambs S, Cimmino A, et al. (2006) A microRNA expression signature of human solid tumors defines cancer gene targets. Proc Natl Acad Sci USA 103: 2257-2261.

38. Hanahan D, Weinberg R A (2011) Hallmarks of cancer: the next generation. Cell 144: 646-674.
39. Ruan K, Fang X, Ouyang G (2009) MicroRNAs: novel regulators in the hallmarks of human cancer. Cancer Lett 285: 116-126.
40. Grammatikakis I, Gorospe M, Abdelmohsen K (2013) Modulation of Cancer Traits by Tumor Suppressor microRNAs. Int J Mol Sci 14: 1822-1842.
41. White N M, Fatoohi E, Metias M, Jung K, Stephan C, et al (2011) Metastamirs: a stepping stone towards improved cancer management. Nat Rev Clin Oncol 8: 75-84.
42. Cho W C (2007) OncomiRs: the discovery and progress of microRNAs in cancers. Mol Cancer 6: 60.
43. Lee Y S, Dutta A (2009) MicroRNAs in cancer. Annu Rev Pathol 4: 199-227.
44. Foekens J A, Sieuwerts A M, Smid M, Look M P, de Weerd V, et al. (2008) Four miRNAs associated with aggressiveness of lymph node-negative, estrogen receptor-positive human breast cancer. Proc Natl Acad Sci USA 105: 13021-13026.
45. Lu J, Getz G, Miska E A, Alvarez-Saavedra E, Lamb J, et al. (2005) MicroRNA expression profiles classify human cancers. Nature 435: 834-838.
46. Volinia S, Croce C M (2013) Prognostic microRNA/mRNA signature from the integrated analysis of patients with invasive breast cancer. Proc Natl Acad Sci USA 110: 7413-7417.

The invention claimed is:

1. A method for treating or preventing the recurrence of breast cancer in a subject comprising the following steps:
   (i) predicting the risk of recurrence of breast cancer in said subject using a method comprising measuring the expression level of each miRNA of the group consisting of:
   a. miR-149-5p (SEQ ID NO: 1);
   b. miR-10a-5p, (SEQ ID NO: 2);
   c. miR-20b-5p, (SEQ ID NO: 3);
   d. miR-30a-3p (SEQ ID NO: 4); and
   e. miR-342-5p, (SEQ ID NO: 5)
   in a tumor sample obtained from said subject, wherein a decrease in the level of each miRNA in the tumor with respect to expression level in a control sample is indicative of a high risk of recurrence of the breast cancer; and
   (ii) treating said subject if the high risk of recurrence of the breast cancer is indicated, thereby treating or preventing the recurrence of breast cancer in said subject.

2. A method for treating or preventing the recurrence of breast cancer in a subject comprising the following steps:
   (i) predicting chance of survival of said subject using a method comprising measuring level of each miRNA of the group consisting of:
   a. miR-149-5p (SEQ ID NO: 1);
   b. miR-10a-5p, (SEQ ID NO: 2);
   c. miR-20b-5p, (SEQ ID NO: 3);
   d. miR-30a-3p (SEQ ID NO: 4); and
   e. miR-342-5p, (SEQ ID NO: 5)
   in a tumor sample obtained from said subject, wherein a decrease in the level of each miRNA in the tumor with respect to expression level in a control sample is indicative of a low chance of survival of said subject; and
   (ii) treating said subject if the low chance of survival of said subject is indicated, thereby treating or preventing the recurrence of breast cancer in said subject.

3. The method of claim 1, wherein the expression level of each miRNA is measured using a method comprising:
   a. gene profiling;
   b. PCR;
   c. a Northern blot; or
   d. any combination of a, b and c.

4. The method of claim 3, wherein the expression level of each miRNA is measured using a method comprising real-time quantitative PCR.

5. The method according to claim 1, wherein the method is carried out in vitro using an original sample from the subject, and wherein the subject is a human.

6. The method according to claim 1, further comprising normalizing the expression level of each miRNA.

7. A method for treating or preventing the recurrence of breast cancer in a human subject comprising:
   (i) assigning said human subject to one of two groups, wherein the first group comprises human subjects determined as having a high risk of recurrence of breast cancer, and wherein the second group comprises human subjects determined as not having a high risk of recurrence of breast cancer, the method comprising measuring the expression level of each miRNA of the group consisting of:

a. miR-149-5p (SEQ ID NO: 1);
b. miR-10a-5p, (SEQ ID NO: 2);
c. miR-20b-5p, (SEQ ID NO: 3);
d. miR-30a-3p (SEQ ID NO: 4); and
e. miR-342-5p, (SEQ ID NO: 5)
in a tumor sample obtained from said human subject, and assigning said human subject to the first group if the expression level of each miRNA in the tumor sample is decreased with respect to expression level in a control sample and assigning said human subject to the second group if the expression level of each miRNA in the tumor sample is not decreased with respect to expression level in a control sample; and (ii) treating said human subject assigned to the first group, thereby treating or preventing the recurrence of breast cancer in said subject.

8. A kit comprising at least five isolated oligonucleotides, wherein each of the five isolated oligonucleotides are capable of hybridizing under stringent conditions to each of the miRNAs as defined by SEQ ID NOs: 1-5, respectively, or to its corresponding cDNA; and an indicator reference value or a reagent for determining the reference value.

9. The kit of claim 8, wherein the oligonucleotides are immobilized in spots on a surface.

10. The method of claim 1, wherein measuring the expression level of each miRNA is carried out using a kit comprising at least five oligonucleotides, wherein each oligonucleotide is capable of hybridizing under stringent conditions to a miRNA as defined in any one of SEQ ID NOs: 1-5 or its corresponding cDNA.

11. The method of claim 6, wherein the expression level of each miRNA is normalized to the expression level of RNU48 and/or miR-16.

12. The kit of claim 9, wherein the surface is a surface of a microarray.

13. The method of claim 7, wherein the expression level of each miRNA is measured using a method comprising:
a. gene profiling;
b. PCR;
c. a Northern blot; or
d. any combination thereof.

14. The method of claim 13, wherein the expression level of each miRNA is measured using a method comprising real-time quantitative PCR.

15. The method according to claim 13, wherein the method is carried out in vitro using an original sample from the subject, and wherein the subject is a human.

16. The method according to claim 7, further comprising normalizing the expression level of each miRNA.

17. The method of claim 16, wherein the expression level of each miRNA is normalized to the expression level of RNU48 and/or miR-16.

18. The method of claim 1, wherein the subject has had surgery to remove a primary breast tumor.

19. The method of claim 1, wherein treating the subject comprises treating the subject with chemotherapy.

20. The method of claim 3, wherein the expression level of each miRNA is measured using a method comprising gene profiling with a microarray.

21. The method of claim 7, wherein measuring the expression level of each miRNA is carried out using a kit comprising at least five oligonucleotides, wherein each oligonucleotide is capable of hybridizing under stringent conditions to a miRNA as defined in any one of SEQ ID NOs: 1-5 or its corresponding cDNA.

22. The method of claim 7, wherein the subject has had surgery to remove a primary breast tumor.

23. The method of claim 7, wherein treating the subject comprises treating the subject with chemotherapy.

24. The method of claim 13, wherein the expression level of each miRNA is measured using a method comprising gene profiling with a microarray.

25. The kit of claim 8, wherein the reference value is expression level of RNU48 or miR-16.

26. The kit of claim 8, further comprising a reagent for performing PCR.

27. The kit of claim 26, wherein the reagent is a polyT oligonucleotide primer.

28. The kit of claim 8, suitable for performing a Northern blot or microarray analysis.

* * * * *

```
                         SEQUENCE LISTING

<160> NUMBER OF SEQ ID NOS: 16

<210> SEQ ID NO 1
<211> LENGTH: 23
<212> TYPE: RNA
<213> ORGANISM: Homo sapiens

<400> SEQUENCE: 1
ucuggcuccg ugucuucacu ccc                                            23

<210> SEQ ID NO 2
<211> LENGTH: 23
<212> TYPE: RNA
<213> ORGANISM: Homo sapiens

<400> SEQUENCE: 2
uacccuguag auccgaauuu gug                                            23

<210> SEQ ID NO 3
<211> LENGTH: 23
<212> TYPE: RNA
<213> ORGANISM: Homo sapiens

<400> SEQUENCE: 3
caaagugcuc auagugcagg uag                                            23

<210> SEQ ID NO 4
<211> LENGTH: 22
<212> TYPE: RNA
<213> ORGANISM: Homo sapiens

<400> SEQUENCE: 4
cuuucagucg gauguuugca gc                                             22

<210> SEQ ID NO 5
<211> LENGTH: 21
<212> TYPE: RNA
<213> ORGANISM: Homo sapiens

<400> SEQUENCE: 5
aggggugcua ucugugauug a                                              21

<210> SEQ ID NO 6
<211> LENGTH: 107
<212> TYPE: RNA
<213> ORGANISM: Homo sapiens

<400> SEQUENCE: 6
gugcucgcuu cggcagcaca uauacuaaaa uuggaacgau acagagaaga uuagcauggc    60
```

```
cccugcgcaa ggaugacacg caaauucgug aagcguucca uauuuuu        107
```

<210> SEQ ID NO 7
<211> LENGTH: 63
<212> TYPE: RNA
<213> ORGANISM: Homo sapiens

<400> SEQUENCE: 7

```
agugaugaug accccaggua acucugagug ugucgcugau gccaucaccg cagcgcucug    60
acc                                                                 63
```

<210> SEQ ID NO 8
<211> LENGTH: 22
<212> TYPE: RNA
<213> ORGANISM: Homo sapiens

<400> SEQUENCE: 8

```
uagcagcacg uaaauauugg cg                                            22
```

<210> SEQ ID NO 9
<211> LENGTH: 23
<212> TYPE: DNA
<213> ORGANISM: Artificial Sequence
<220> FEATURE:
<223> OTHER INFORMATION: To amplify miR-149-5p

<400> SEQUENCE: 9

```
gggagtgaag acacggagcc aga                                           23
```

<210> SEQ ID NO 10
<211> LENGTH: 23
<212> TYPE: DNA
<213> ORGANISM: Artificial Sequence
<220> FEATURE:
<223> OTHER INFORMATION: To amplify miR-10a-5p

<400> SEQUENCE: 10

```
cacaaattcg gatctacagg gta                                           23
```

<210> SEQ ID NO 11
<211> LENGTH: 23
<212> TYPE: DNA
<213> ORGANISM: Artificial Sequence
<220> FEATURE:
<223> OTHER INFORMATION: To amplify miR-20b-5p

<400> SEQUENCE: 11

```
ctacctgcac tatgagcact ttg                                           23
```

<210> SEQ ID NO 12
<211> LENGTH: 22
<212> TYPE: DNA
<213> ORGANISM: Artificial Sequence
<220> FEATURE:
<223> OTHER INFORMATION: To amplify miR-30a-3p

<400> SEQUENCE: 12

```
gctgcaaaca tccgactgaa ag                                            22
```

<210> SEQ ID NO 13
<211> LENGTH: 21
<212> TYPE: DNA
<213> ORGANISM: Artificial Sequence
<220> FEATURE:

```
<223> OTHER INFORMATION: To amplify miR-342-5p

<400> SEQUENCE: 13
tcaatcacag atagcacccc t                                              21

<210> SEQ ID NO 14
<211> LENGTH: 21
<212> TYPE: DNA
<213> ORGANISM: Artificial Sequence
<220> FEATURE:
<223> OTHER INFORMATION: To amplify RNU6B

<400> SEQUENCE: 14
aaaaatatgg aacgcttcac g                                              21

<210> SEQ ID NO 15
<211> LENGTH: 21
<212> TYPE: DNA
<213> ORGANISM: Artificial Sequence
<220> FEATURE:
<223> OTHER INFORMATION: To amplify RNU48

<400> SEQUENCE: 15
ggtcagagcg ctgcggtgat g                                              21

<210> SEQ ID NO 16
<211> LENGTH: 22
<212> TYPE: DNA
<213> ORGANISM: Artificial Sequence
<220> FEATURE:
<223> OTHER INFORMATION: To amplify miR-16-5p

<400> SEQUENCE: 16
cgccaatatt tacgtgctgc ta                                             22
```